US010588957B2

(12) United States Patent
Scholz et al.

(10) Patent No.: US 10,588,957 B2
(45) Date of Patent: Mar. 17, 2020

(54) METHOD FOR THE PRODUCTION OF STABILE VACCINES

(71) Applicant: LEUKOCARE AG, Martinsried/München (DE)

(72) Inventors: Martin Scholz, München (DE); Jens Altrichter, Kavelstorf (DE); Kristina Kemter, München (DE); Regina Scherliess, Kiel (DE); Hartwig Steckel, Kiel (DE)

(73) Assignee: LEUKOCARE AG, Martinsried/München (DE)

( * ) Notice: Subject to any disclaimer, the term of this patent is extended or adjusted under 35 U.S.C. 154(b) by 699 days.

(21) Appl. No.: 15/031,329

(22) PCT Filed: Oct. 24, 2014

(86) PCT No.: PCT/EP2014/072871
§ 371 (c)(1),
(2) Date: Apr. 22, 2016

(87) PCT Pub. No.: WO2015/059284
PCT Pub. Date: Apr. 30, 2015

(65) Prior Publication Data
US 2018/0339036 A1  Nov. 29, 2018

(30) Foreign Application Priority Data
Oct. 25, 2013 (EP) .................................. 13190397

(51) Int. Cl.
| A61K 38/16 | (2006.01) |
| A61K 38/00 | (2006.01) |
| C07K 1/00 | (2006.01) |
| C12P 21/06 | (2006.01) |
| C12P 19/30 | (2006.01) |
| A61K 39/145 | (2006.01) |
| A61K 39/12 | (2006.01) |
| A61P 31/16 | (2006.01) |
| A61K 9/08 | (2006.01) |
| A61K 47/18 | (2017.01) |
| A61K 47/26 | (2006.01) |
| A61K 47/36 | (2006.01) |

(52) U.S. Cl.
CPC .............. *A61K 39/145* (2013.01); *A61K 9/08* (2013.01); *A61K 39/12* (2013.01); *A61K 47/183* (2013.01); *A61K 47/26* (2013.01); *A61K 47/36* (2013.01); *A61P 31/16* (2018.01); *C12N 2760/16134* (2013.01); *C12N 2760/16151* (2013.01); *C12N 2760/16251* (2013.01); *C12N 2760/16351* (2013.01)

(58) Field of Classification Search
CPC ........ C07K 9/00; C07K 14/505; C07K 1/006; C07K 1/13; C07K 1/1077
See application file for complete search history.

(56) References Cited

U.S. PATENT DOCUMENTS

| 2008/0003657 A1* | 1/2008 | Dietzschold ......... C07K 14/005 435/235.1 |
| 2011/0081380 A1 | 4/2011 | Francon et al. |
| 2011/0200635 A1* | 8/2011 | Banzhoff ............. A61K 39/145 424/206.1 |

FOREIGN PATENT DOCUMENTS

| CN | 101631563 A | 1/2010 |
| CN | 101679954 A | 3/2010 |
| CN | 102245203 A | 11/2011 |
| CN | 102448992 A | 5/2012 |
| EP | 2119451 A1 * | 11/2009 |
| WO | WO-2004/073652 A2 | 9/2004 |
| WO | WO-2009/014774 A1 | 1/2009 |
| WO | WO2009014774 * | 1/2009 |
| WO | WO-2010/115835 A2 | 10/2010 |
| WO | WO2010115835 * | 10/2010 |
| WO | WO-2013/001034 A1 | 1/2013 |
| WO | WO-2013/001044 A1 | 1/2013 |
| WO | WO-2015/059284 A1 | 4/2015 |

OTHER PUBLICATIONS

Zaharoff et al., "Chitosan Solution Enhances Both Humoral and Cell-Mediated Immune Responses to Subcutaneous Vaccination," Vaccine, 25(11): 2085-2094 (2007).
International Search Report and Written Opinion of the International Searching Authority, dated Dec. 16, 2014, from corresponding International Application No. PCT/EP2014/072871.
Wang et al., "Intranasal immunization with live attenuated influenza vaccine plus chitosan as an adjuvant protects mice against homologous and heterologous virus challenge," Arch Virol, 157:1451-61 (2012).
Kanojia et al., "Developments in the formulation and delivery of spray dried vaccines," Hum Vacc Immunother, 13:2364-2378 (2017).

* cited by examiner

*Primary Examiner* — Barry A Chestnut
(74) *Attorney, Agent, or Firm* — Foley Hoag LLP

(57) ABSTRACT

The present invention relates to a method for producing stabilised vaccines, the method comprising: (a) mixing antigens with a solution comprising: (i) chitosan; (ii) at least three different amino acids and/or at least one dipeptide or tripeptide; and (iii) a sugar; and (b) drying the mixture obtained in (a).

14 Claims, 18 Drawing Sheets

Figure 1A:
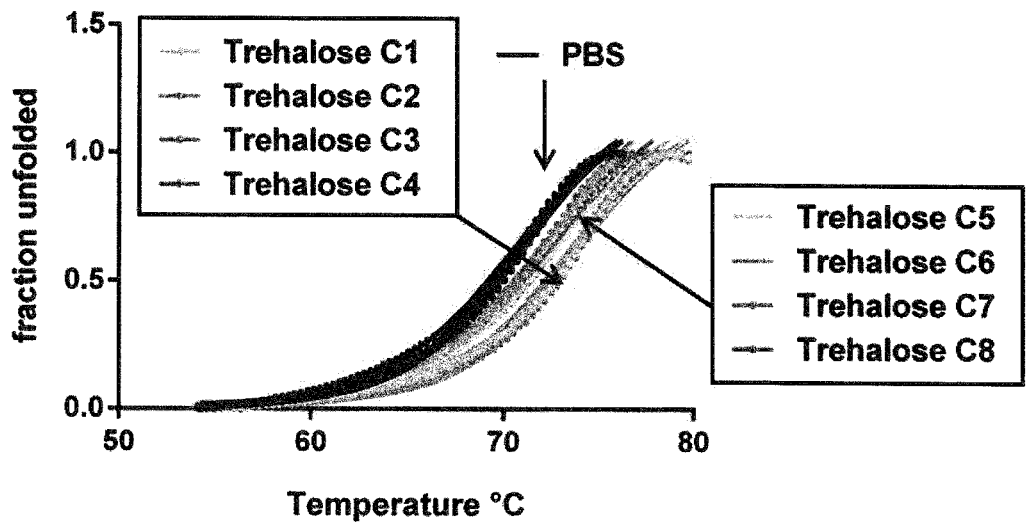
Figure 1B:
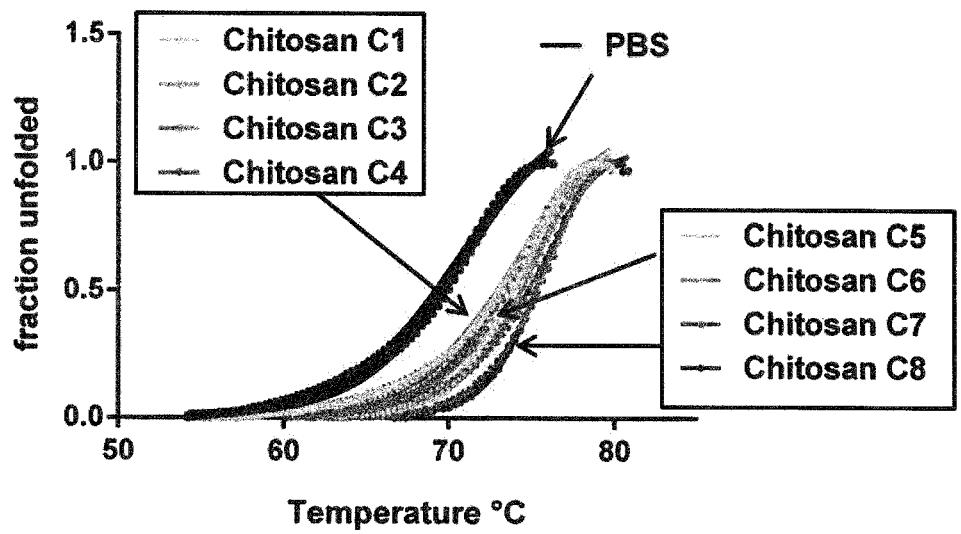
Figure 1C:
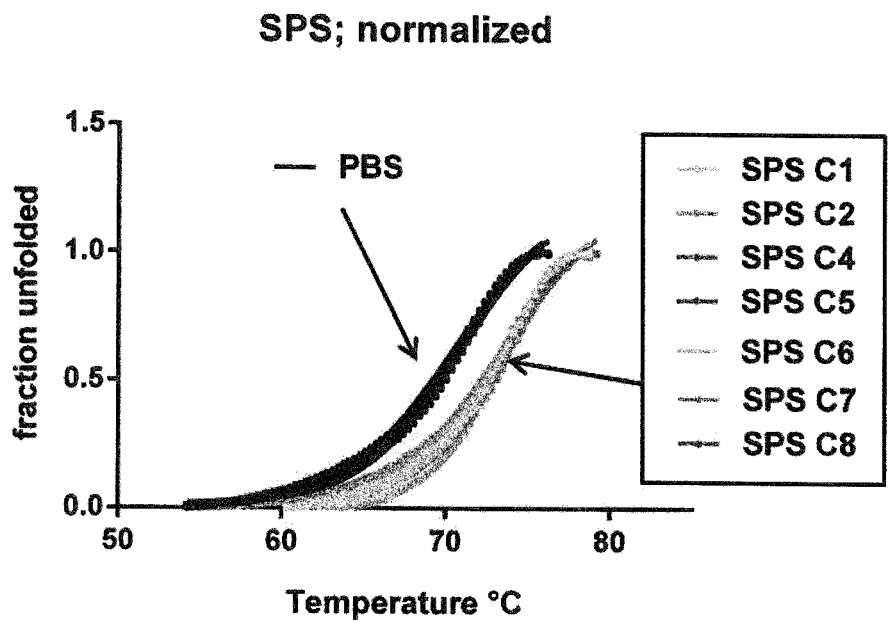
Figure 1D:
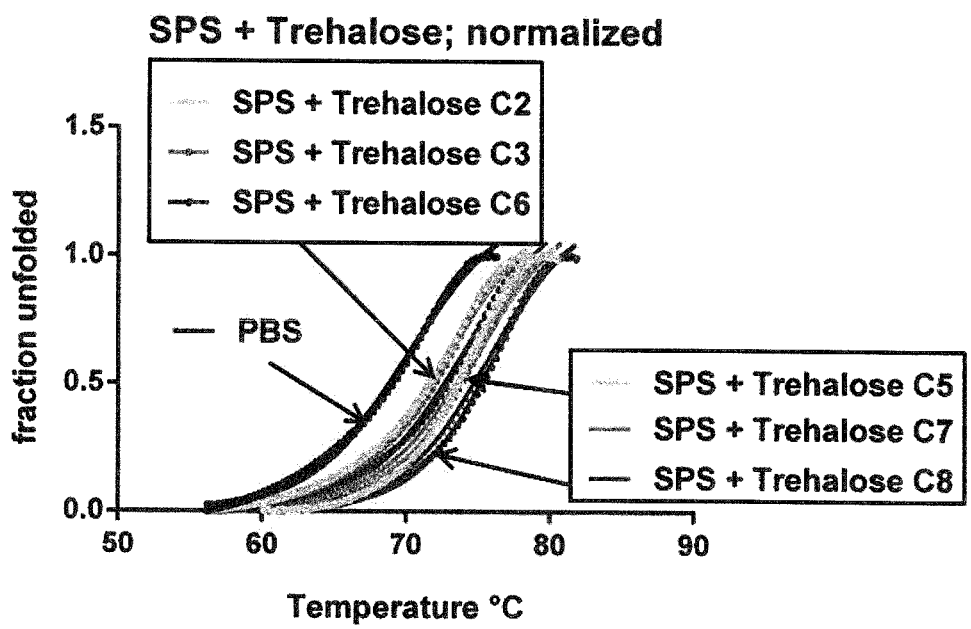
Figure 1E:
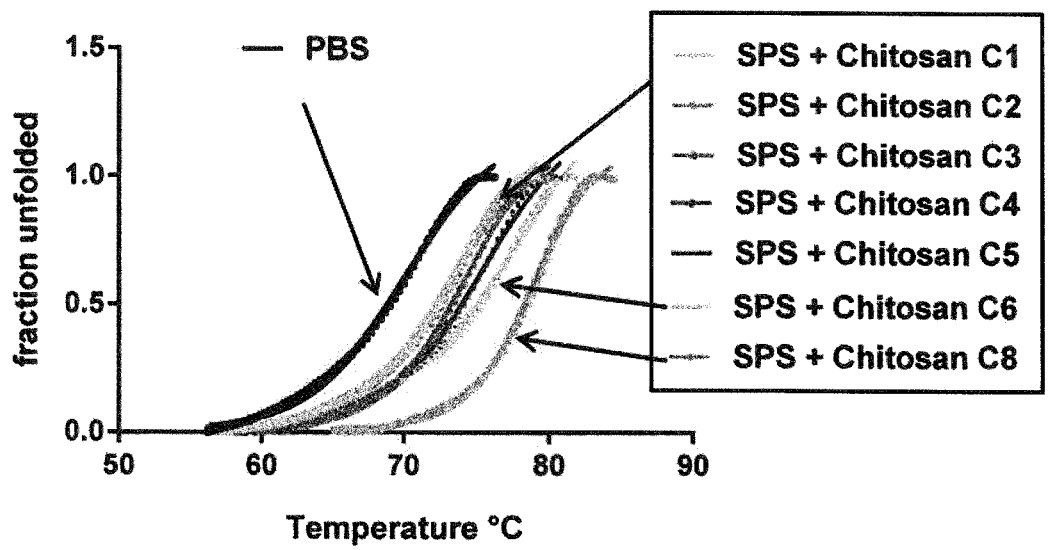
Figure 1F:
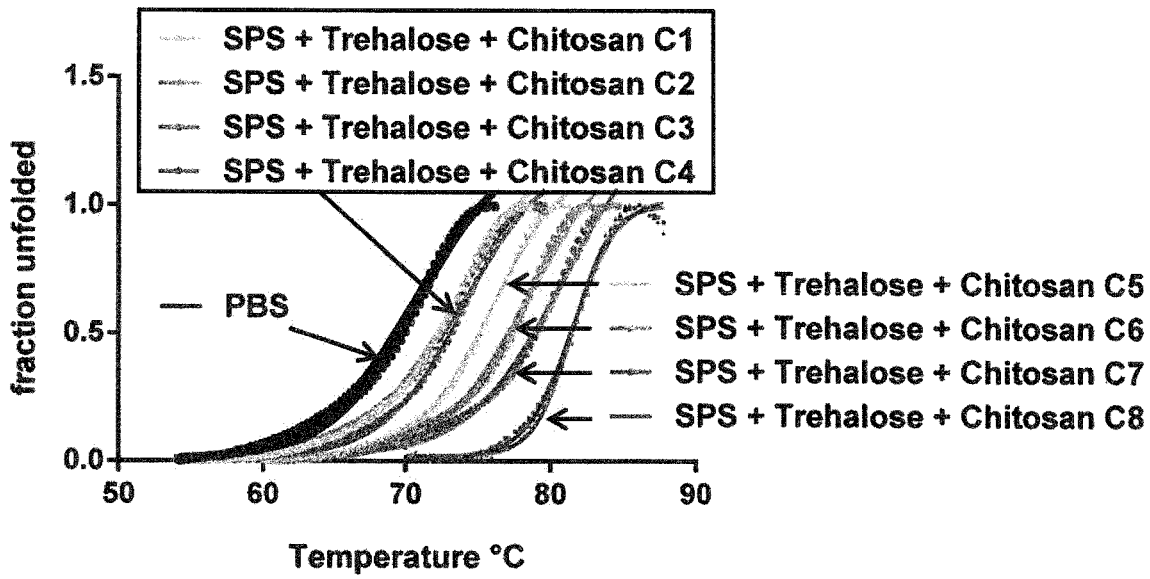
Figure 1G:
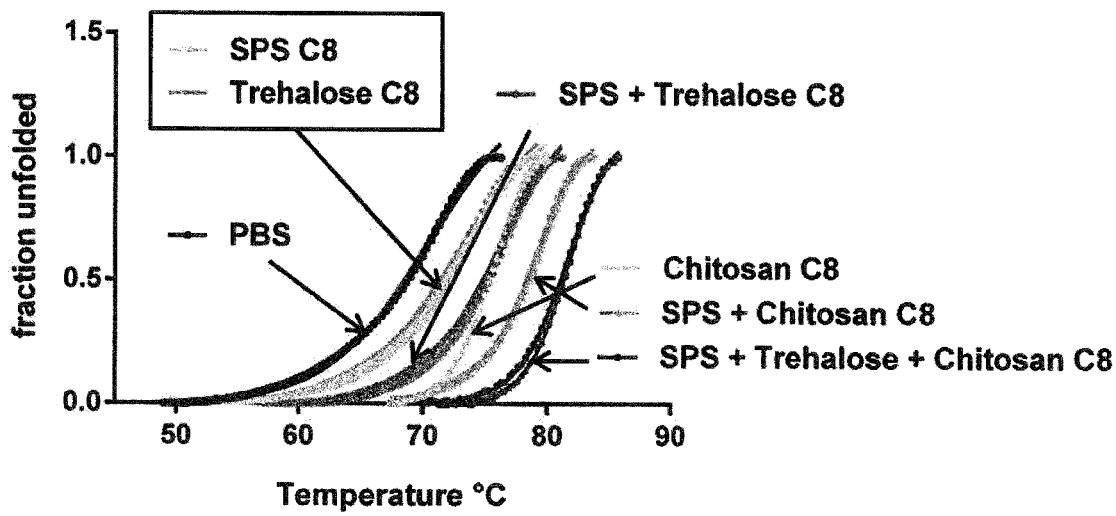

Comparison of the excipients and excipient mixtures

METHOD FOR THE PRODUCTION OF STABILE VACCINES

RELATED APPLICATIONS

This application is a § 371 national-stage application based on PCT Application PCT/EP2014/072871, filed Oct. 24, 2014, which claims the benefit of priority to EP 13190397, filed Oct. 25, 2013.

The present invention relates to a method for producing stabilised vaccines, the method comprising: (a) mixing antigens with a solution comprising: (i) chitosan; (ii) at least three different amino acids and/or at least one dipeptide or tripeptide; and (iii) a sugar; and (b) drying the mixture obtained in (a).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Today, major challenges in the field of vaccination are to develop thermostable vaccines and to establish needle-free vaccination strategies to fight viral diseases, even in developing countries [1], which also is one of the strategic aims of the WHO Global Immunization Vision and Strategy [2]. Furthermore, to be better prepared for pandemic outbreaks, stockpiles of stable vaccine formulations are required [3]. For example, in 2011, 16 million doses of the anti-influenza A vaccines that were produced in prospect for a possible H1N1 outbreak had to be destroyed by the German government due to limited shelf live. The costs for the unused doses were immense.

Liquid preparations face a high risk of instability during storage because of high molecular mobility and increased likelihood of chemical reactions and physical instability [4]. For this reason, many liquid vaccine preparations need to be stored and transported under refrigeration and have a short shelf life. For liquid antigen preparations, stability is often enhanced by selection of pH-buffering salts and the use of amino acids for stabilisation [5, 6].

The stability of such preparations, especially their thermal stability, can be greatly increased by drying the antigens. Thus, one approach to enhance storage stability that is commonly applied is freeze-drying, thereby minimising molecular mobility and the risk of intermolecular reactions. This approach requires that the antigen is stabilised during both the step of freezing (cryoprotection) and the subsequent step of drying (lyoprotection) [7]. This can, for example, be achieved by an exchange of water with other hydrophilic molecules which may replace it as hydrogen bond forming partner. Another possibility is the formation of a sugar glass matrix, which can also be used to stabilise vaccine preparations [8].

This general principle can also be transferred to other drying techniques, such as spray-freeze drying or spray-drying. Spray-drying is often the method of choice, as it avoids the freezing step and requires lower energy costs as compared to lyophilisation. Spray-drying has also been shown to be a particularly advantageous drying procedure that is suitable for biomolecules, due to the short contact time with high temperature and its special process control [9-12]. Thus, spray-drying being a process resulting in a dispersible dry powder in just one step is often favoured to freeze drying for biomolecules [13]. The products obtained can be designed to have good dispersion characteristics as well as low agglomeration and adhesive tendencies to allow powder handling, packaging and efficient re-dispersion upon contact with water or buffer. This is especially true for spray drying which, accordingly, is particularly suitable for bulk production of large amounts of vaccines [14]. However, antigens processed by spray-drying are exposed to high temperatures and mechanical stress, which may potentially result in the loss of molecular integrity and efficacy. Therefore, antigen protection is nonetheless required even during this one-step production approach.

Another hurdle in vaccine production is the sterilisation of vaccine preparations without significant loss of material. Standard sterile filtrations of biomolecules leave the risk of contamination during aseptic fill and finish [15] and may hence lead to significant economic loss. Therefore, the need for technologies that enable terminal sterilisation of biomolecules increases [16-18]. Currently, irradiation is not considered a valid sterilisation protocol for biologics since it is associated with high energy input and increases the risk for chemical and physical modifications entailing misfolding, formation of aggregates and fragmentation [19-21]. Especially, aggregates may lead to modified immunogenicity of therapeutically applied biologics [22]. Other sterilisation techniques such as heat sterilisation or autoclaving are inappropriate due to extensive heat stress of the product.

Overall, the development of highly stable terminally sterilised powder vaccines, including split virus vaccines such as e.g. influenza A, has not yet been achieved. The main bottlenecks in this development are to obtain sufficient amounts of vaccine powder, to sterilise the vaccine powder, to avoid unappreciated antigen modifications and to avoid loss of specific immunogenicity and thus efficacy.

Accordingly, despite the fact that a lot of research has been invested into providing suitable methods for improving the stability of vaccines during production, sterilisation and storage, there is still a need to provide improved methods for producing stabilised vaccines that can be stored for prolonged periods of time and under various stress conditions.

This need is addressed by the provision of the embodiments characterised in the claims.

Accordingly, the present invention relates to a method for producing stabilised vaccines, the method comprising: (a) mixing antigens with a solution comprising: (i) chitosan; (ii) at least three different amino acids and/or at least one dipeptide or tripeptide; and (iii) a sugar; and (b) drying the mixture obtained in (a).

In accordance with the present invention, a method is provided for producing vaccines that are stable, in particular during the production, sterilisation and storage process. The term "stabilised", in accordance with the present invention, relates to the full or partial maintenance of the biological, immunogenic activity of the vaccine, i.e. its ability to stimulate the immune system of a subject, such as e.g. a human subject, to recognize it as foreign, destroy it, and subsequently enable the immune system to protect the subject against the disease for which the vaccine has been developed. The vaccine is considered to be stable if it maintains at least 50% of the activity that the antigen employed for producing the vaccine has prior to being employed in the claimed production method. More preferably, the vaccine maintains at least 60%, such as e.g. at least 70%, more preferably at least 80%, even more preferably at least 90%, such as e.g. at least 95% of the activity that the antigen employed for producing the vaccine has prior to being employed in the claimed production method. More preferably, the vaccine maintains at least 98%, such as e.g. at least 99% and most preferably 100% of the activity that the antigen employed for producing the vaccine has prior to being employed in the claimed production method. Means to test whether a vaccine is stabilised are well known to the skilled person and include, without being limiting, testing in hemagglutination assays (HA), radioimmunoassays, biosensor analysis, immunoprecipitation or ELISA assaying. Exemplary methods are shown in the appended examples.

In a first step of the method of producing stabilised vaccines of the present invention, antigens are mixed with a solution comprising the recited stabilising excipients.

Suitable antigens for vaccine preparation are well known in the art and the considerations for choosing an antigen for vaccine production commonly applied in the art apply mutatis mutandis with regard to choosing a suitable antigen for vaccine production in accordance with the present invention. Accordingly, antigens already available in the art, as well as novel antigens, may be employed in the claimed method.

Typically, antigens are proteins and polysaccharides, but may also be lipids or nucleic acids, which are, however, only antigenic when combined with proteins and polysaccharides. Antigens are often derived from parts of bacteria, viruses, and other microorganisms, such as e.g. their coats, capsules, cell walls, flagella, fimbrae, or toxins. Antigens can also be non-microbial, such as e.g. self-antigens or exogenous (non-self) antigens such as pollen, egg white, or proteins from transplanted tissues/organs or on the surface of transfused blood cells.

In accordance with the present invention, the term "antigens" includes, without being limiting, (i) antigens represented by one particular molecular type of antigen, such as e.g. one particular protein; (ii) antigen mixtures of different molecular types of antigen, such as e.g. a mixture of different proteins or a mixture of proteins with polysaccharides; as well as (iii) antigen preparations comprising further components, such as e.g. in split-virus antigens, which are preparations wherein a virus has been disrupted by e.g. a detergent, or another method, without further removal of other viral components.

Accordingly, antigens may for example be subunit antigens, virus like particles, life viruses as well as viral vectors such as e.g. MVA or Adenovirus.

In accordance with the present invention, the antigens are mixed with a solution comprising the recited recipients. This solution can be an aqueous or a non-aqueous solution. In the context of the present invention, the term "aqueous solution" refers on one hand to water but extends on the other hand also to buffered solutions and hydrophilic solvents miscible with water, thus being able to form a uniform phase. Examples for aqueous solutions comprise, but are not limited to water, methanol, ethanol or higher alcohols as well as mixtures thereof. Examples for non-aqueous solvents comprise, without being limiting, dimethylsulfoxide (DMSO), ethylbenzene, and other polar solvents.

Preferably, the solution is an "aqueous solution" and, more preferably, the solvent in the solution in accordance with the method of the invention is water.

The term "comprising" in the context of the solution according to the method of the invention denotes that further components can be present in the solution. Non-limiting examples of such further components include saponines, as described herein below, as well as e.g., water, buffers or solvents. Preferably, the solution does not contain any proteins. More preferably, the solution consists of: (i) chitosan-HCl; (ii) at least three different amino acids and/or at least one dipeptide or tripeptide; (iii) a sugar and (iv) at least one saponine. Even more preferably, the solution consists of: (i) chitosan-HCl; (ii) at least three different amino acids and/or at least one dipeptide or tripeptide; and (iii) a sugar. It is further preferred that the solution has a pH value in the range of 6 to 8, more preferably the solution has a pH value of 7.

Chitosan is a polysaccharide composed of randomly distributed β-(1-4)-linked D-glucosamine (deacetylated unit) and N-acetyl-D-glucosamine (acetylated unit). Chitosan is produced commercially by deacetylation of chitin, which is the structural element in the exoskeleton of crustaceans and the cell walls of fungi. The process causes changes in molecular weight and a degree of deacetylation of the product and degradation of nutritionally valuable proteins. The molecular weight of chitosan is between 3800 and 20.000 Daltons. The degree of deacetylation (% DD) can be determined by NMR spectroscopy, and the % DD in commercial chitosans ranges from 60 to 100%. Chitosan can be obtained from commercial suppliers, such as e.g. Heppe Medical Chitosan GmbH, FMC Biopolymer, Sigma Aldrich and others.

The term chitosan, as used herein, encompasses salts and derivatives of chitosan, such as e.g. the salts chitosan-HCl, chitosan-glutamate, chitosan-aspartate, chitosan-citrate, chitosan-acetate, carboxymethyl-chitosan and chitosan derivatives such as trimethyl chitosan, zwitterionic chitosan, and glycated chitosan.

It will be appreciated that the chitosan has to be present in soluble form in the solution. The skilled person knows how to choose a suitable chitosan depending on the solution employed. For example, where the solution is an aqueous solution, or where the solution has a pH of 7, the preferred chitosan to be employed is chitosan-HCl.

Preferred amounts of chitosan, and in particular of chitosan-HCl, to be employed are between 0.01 and 15 mg/ml, preferably between 0.1 and 10 mg/ml, more preferably between 0.5 and 5 mg/ml, even more preferably between 1 and 3 mg/ml and most preferably the amount is 2 mg/ml.

The term "amino acid", in accordance with the present invention, relates to organic molecules that have a carboxylic acid group, an amino group and a side-chain that varies between different amino acids. Amino acids are the essential building blocks of proteins. In accordance with the present invention, the term "amino acid" refers to free amino acids which are not bound to each other to form oligo- or polymers such as dipeptides, tripeptides, oligopeptides or proteins (also referred to herein as polypeptides).

The amino acids comprised in the solution of the present invention can be selected from naturally occurring amino acids as well as artificial amino acids or derivatives of these naturally occurring or artificial amino acids.

Naturally occurring amino acids are e. g. the 20 proteinogenic amino acids glycine, proline, arginine, alanine, asparagine, aspartic acid, glutamic acid, glutamine, cysteine, phenylalanine, lysine, leucine, isoleucine, histidine, methionine, serine, valine, tyrosine, threonine and tryptophan. Other naturally occurring amino acids are e. g. carnitine, creatine, creatinine, guanidinoacetic acid, ornithine, hydroxyproline, homocysteine, citrulline, hydroxylysine or beta-alanine. Artificial amino acids are amino acids that have a different side chain length and/or side chain structure and/or have the amine group at a site different from the alpha-C-atom. Derivates of amino acids include, without being limiting, n-acetyl-tryptophan, phosphonoserine, phosphonothreonine, phosphonotyrosine, melanin, argininosuccinic acid and salts thereof and DOPA. In connection with the present invention, all the terms also include the salts of the respective amino acids.

In accordance with the present invention, three or more amino acids, which differ from each other, are comprised in the solution. For example, the term "at least three different amino acids" also relates to at least four different amino acids, such as at least five, at least six, at least seven, at least eight, at least nine, at least ten different amino acids or more, such as at least eleven, at least 12, at least 13, at least 14, at least 15, at least 16, at least 17 or at least 18 different amino acids. The term further encompasses exactly three, exactly four, exactly five, exactly six, exactly seven, exactly eight, exactly nine, exactly ten, exactly eleven, exactly 12, exactly 13, exactly 14, exactly 15, exactly 16, exactly 17 or exactly 18 different amino acids. It will be readily understood by a person skilled in the art that when referring to an amino acid herein, more than one molecule of said amino acid are intended. Thus, the recited amount of different amino acids is intended to limit the amount of different types of amino acids, but not the number of molecules of one type of amino acid. For example the term "three different amino acids", refers to three different types of amino acids, wherein the amount of each individual amino acid is not particularly limited. Preferably, the number of different amino acids does not exceed 18 different amino acids.

The term "dipeptide or tripeptide", as used herein, relates to peptides consisting of two or three amino acids, respectively. Exemplary dipeptides are glycylglutamine (Gly-Gln), glycyltyrosine (Gly-Tyr), alanylglutamine (Ala-Gln) and glycylglycine (Gly-Gly). Further non-limiting examples of naturally occurring dipeptides are carnosine (beta-alanyl-L-histidine), N-acetyl-carnosine (N-acetyl-(beta-alanyl-L-histidine), anserine (beta-alanyl-N-methyl histidine), homoanserine (N-(4-aminobutyryl)-L-histidine), kyotorphin (L-tyrosyl-L-arginine), balenine (or ophidine) (beta-alanyl-N tau-methyl histidine), glorin (N-propionyl-γ-L-glutamyl-L-ornithine-δ-lac ethyl ester) and barettin (cyclo-[(6-bromo-8-en-tryptophan)-arginine]). Examples of artificial dipeptides include, without being limiting, aspartame (N-L-a-aspartyl-L-phenylalanine 1-methyl ester) and pseudoproline.

Exemplary tripeptides are glutathione (γ-glutamyl-cysteinyl-glycine) and its analogues ophthalmic acid (L-γ-glutamyl-L-α-aminobutyryl-glycine) as well as norophthalmic acid (y-glutamyl-alanyl-glycine). Further non-limiting examples of tripeptides include isoleucine-proline-proline (IPP), glypromate (Gly-Pro-Glu), thyrotropin-releasing hormone (TRH, thyroliberin or protirelin: L-pyroglutamyl-L-histidinyl-L-prolinamide), melanostatin (prolyl-leucyl-glycinamide), leupeptin (N-acetyl-L-leucyl-L-leucyl-L-argininal) and eisenin (pGlu-Gln-Ala-OH). It is preferred that the at least one di- or tripeptide and more preferred all di- or tripeptides, when used in connection with medical applications, do not exert any pharmacological properties.

In accordance with the present invention, the solution may alternatively, or additionally, comprise one or more di- or tripeptides. The term "at least one dipeptide or tripeptide" also relates to at least two di- or tripeptides, such as at least three, at least four, at least five, at least six, at least seven, at least eight or at least nine di- or tripeptides. The term further encompasses exactly one, exactly two, exactly three, exactly four, exactly five, exactly six, exactly seven, exactly eight or exactly nine di- or tripeptides. Where more than one di- or tripeptide is comprised in the solution, a mixture of dipeptides and tripeptides is explicitly envisaged herein. The number of di- and tripeptides can be selected independently of each other, e.g. the solution may comprise two dipeptides and three tripeptides. It will be readily understood by the skilled person that when referring to a certain number of di- and tripeptides herein, said number is intended to limit the amount of different types of di- and tripeptides, but not the number of molecules of one type of dipeptide or tripeptide. Thus, for example the term "four dipeptides or tripeptides", refers to four different types of dipeptides and/or tripeptides, wherein the amount of each individual di- and/or tripeptide is not particularly limited. Preferably, the number of (different) di- or tripeptides does not exceed nine di- or tripeptides.

Preferably, the total amount of all amino acids, dipeptides and/or tripeptides (that is the sum of all of these components in the solution) to be employed is between 0.1 and 160 mg/ml, preferably between 10 and 120 mg/ml, more preferably between 40 and 100 mg/ml, even more preferably between 60 and 90 mg/ml and most preferably the amount is 80 mg/ml.

In accordance with the present invention, the solution further comprises a sugar. Any types of sugars, i.e. the monosaccharide, disaccharide or oligosaccharide forms of carbohydrates as well as sugar alcohols, are encompassed by said term. Examples of sugars commonly used in methods of vaccine formulations include, without being limiting, saccharose, trehalose, sucrose, glucose, lactose, sorbitol or mannitol. The solution comprises preferably between 0.1 mg/ml to 300 mg/ml sugar, more preferably between 80 mg/ml to 200 mg/ml sugar, even more preferably between 100 mg/ml to 180 mg/ml sugar and most preferably 160 mg/ml sugar. It is explicitly envisaged that the term "a sugar" is not limited to one type of sugar, i.e. said term also encompasses one or more types of sugar, such as e.g. a mixture of two different types of sugar. Preferably, the term refers to only one type of sugar, such as e.g. trehalose. Where a mixture of different types of sugar is employed, the above recited preferred amounts refer to the sum of all sugars in the solution.

The term "dried preparation", as used herein, refers to a preparation in which the liquid content has been removed or reduced. Suitable methods for drying an antigen preparation include, without being limiting, lyophilisation (freeze-drying), spray-drying, spray-freeze drying, air drying or vacuum drying or supercritical drying.

The liquid content is considered to have been reduced if the liquid is reduced to less than 20% of the volume, such as for example less than 10%, such as for example less than 8%, more preferably less than 7% of the volume, such as less than 5% or less than 1%. Even more preferably, the liquid is reduced to 0.5% or less. Most preferably, the liquid is completely reduced, i.e. the remaining liquid is 0% as determined by standard methods.

In accordance with the method of the present invention, a dry vaccine is obtained. It is particularly preferred that the vaccine is a powder vaccine. In the case of spray drying, the resulting dried vaccine is obtained in the form of a powder. In those cases where the dry vaccine is not obtained as a powder, but in instead in the form of e.g. a dried cake, the skilled person is aware of how to further modify the vaccine in order to obtain a powder.

The reduced water content reduces molecular mobility within the product and hence minimises/reduces/inhibits degradation and, thus, offers additional protection of the antigens during storage. Furthermore, surface antigens as well as proteins necessary for host cell binding that are present on the envelope or coat of e.g. a virus, subunit antigens, virus like particles, life viruses, viral vectors, e.g. MVA, Adenovirus etc. are protected by the inventive solution during the drying step, as well as a potential subsequent sterilisation step, thus maintaining the antigenicity of the antigens. Accordingly, after reconstitution, the antigens represent vaccines.

In a further preferred embodiment of the method of the invention, the method further comprises the step of subsequently storing the stabilised vaccine at a temperature selected from about −90° C. to about 45° C. More preferably, the stabilised vaccine is subsequently stored at a temperature range selected from the group consisting of about −90° C. to about −70° C., about −30° C. to about −10° C., about 1° C. to about 10° C., about 15° C. to about 25° C. and about 30° C. to about 43° C. Even more preferably, the stabilised vaccine is subsequently stored at a temperature range selected from the group consisting of about −85° C. to about −75° C., about −25° C. to about −150° C., about 2° C. to about 8° C. and about 20° C. to about 40° C. Most preferably, the stabilised viruses or bacteria are subsequently stored at a temperature selected from about −80° C., about −20° C., room temperature, about 4° C. and about 25° C.

The term "about", as used herein, encompasses the explicitly recited values as well as small deviations therefrom. In other words, a temperature of "about −90° C." includes, but does not have to be exactly the recited amount of −90° C. but may differ by several degrees, thus including for example −91° C., −92° C., −89° C. or −88° C. The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about".

In accordance with the present invention, a preclinical safety and efficacy study was conducted to evaluate new vaccine formulations regarding thermal resistance, storage stability and resistance against irradiation-mediated damage. As is shown in the appended examples, it could surprisingly be demonstrated that vaccine formulation by drying is a feasible strategy to produce highly stable and efficacious vaccine powders, such as e.g. influenza A vaccine powders. These vaccines were even shown to be suitable for terminal sterilisation (e.g. β-irradiation).

The efficacy of the novel antigen stabilizing and protecting solutions (also referred to herein as "the inventive solution") was evaluated with regard to protection of H1N1 split virus antigen under experimental conditions in vitro and in vivo. Original vaccine or vaccine that was re-buffered with the inventive solution was spray-dried and terminally sterilised by irradiation with 25 kGy (e-beam) and antigen integrity was monitored by SDS-PAGE, dynamic light scattering, size exclusion chromatography and functional hemagglutination assays. In vitro screening experiments revealed a number of highly stable compositions containing chitosan.

As discussed herein above, there are several antigen stability issues to address during the development of dried vaccines, in particular dry powder vaccines. For example, spray-drying is associated with high temperature and mechanical shear stress for biomolecules, such as proteins, that may result in protein aggregation and degradation [3]. Stabilizing excipients should, therefore, particularly have stabilizing efficacy against thermal stress.

Typically, before starting the development of a stable vaccine composition, a pre-screening by Differential Scanning Fluorimetry (DSF) is carried out to determine the stabilizing potency of stabilizing excipients against thermal stress using a common model protein [23, 24]. This fluorescence-based thermal shift assay is a reliable measure to monitor a protein conformational stability upon thermal denaturation and an excellent to screen for conditions that stabilize a protein or an antigen. As a probe, an environmentally sensitive fluorescence dye whose quantum yield increases upon binding to increasingly exposed hydrophobic protein regions upon unfolding is applied to monitor thermal unfolding of a protein. The comparison of the protein melting temperature $T_m$, the temperature at the equilibrium where the concentrations of folded and unfolded protein are equal, in different stabilizing environments of the protein is a convenient method to evaluate the stabilising effect of the analysed excipient mixtures on the protein stability. Using such an approach, it could be surprisingly shown that the addition of chitosan, here the salt chitosan-HCl, to a mixture of stabilizing excipients with a model protein resulted in a remarkable shift of the thermal profiles of the model proteins to higher temperatures, which could not be achieved with either the excipients alone or a mixture of the stabilizing excipients.

Chitosan has an antibacterial effect [34], which renders it a particular advantageous addition to vaccine preparations during the entire preparation process. Moreover, chitosan has previously been reported to have an adjuvant effect [25, 27] and to improve vaccination efficacy due to improved bio-adhesion of the vaccine on the mucosa, to increase bioavailability and to boost mucosal immune response [30-33]. This renders its addition to vaccine preparations further advantageous, because less acceptable additional components such as e.g. the bactericide thiomersal or squalen as part of the adjuvant AS03 no longer need to be included in the vaccine. Accordingly, the addition of chitosan during the preparation process of dried vaccines not only avoids the use of unwanted bactericides and adjuvants, but additionally provides a surprising stabilising effect on the vaccine; see example 2, 3, 4 and 5.

Storage data revealed high stability of protected vaccines, i.e. after storage of the spray dried vaccine with and without irradiation, no relevant loss of stability was monitored over three months storage period at 2 to 8° C. (representing normal refrigerated storage conditions) or at 25° C./60% relative humidity (representing accelerated stability storage conditions) (example 4). Data from 3 months storage at 25° C. thus provide evidence for real time storage stability of 12 months at 2 to 8° C.

Additional in vivo experiments revealed that animals receiving original vaccine exhibited the expected levels of seroconversion after 21 days (prime) and 48 days (boost) as assessed by hemagglutination inhibition and microneutralisation assays. However, animals vaccinated with spray-dried and irradiated vaccine failed to exhibit seroconversion after 21 days. This loss of activity could be prevented when the vaccines where protected by the inventive solution (also referred to herein as "the protected vaccines"), resulting in similar seroconversion levels to those vaccinated with original vaccine. Boost immunisation with protected vaccine resulted in a strong increase in seroconversion but had only minor effects in animals treated with unprotected vaccine.

This finding is particularly surprising, as chitosan has been described in the art as being particularly instable when exposed to radiation, such as e.g. γ-radiation [28]. As shown in the appended examples, chitosan nonetheless was found to provide a stabilising effect during the production and subsequent sterilisation of antigens.

Thus, it could be shown that spray-drying and terminal sterilisation of vaccines, such as e.g. H1N1 split virus vaccine, is feasible in the presence of the protective solution of the invention. To the inventors' best knowledge, no successful preclinical data with terminally sterilised dry-powder influenza A vaccine has been reported so far. These findings indicate the potential utility of such formulated vaccines e.g. for needle-free vaccination routes and delivery to countries with uncertain cold chain facilities, thereby overcoming the presently encountered major drawbacks in vaccine manufacturing and distribution, i.e. the need for cooled storage and the impossibility of terminal sterilisation.

In an alternative embodiment, the present invention relates to a method for producing stabilised (poly)peptides, the method comprising: (a) mixing (poly)peptides with a solution comprising: (i) chitosan; (ii) at least three different amino acids and/or at least one dipeptide or tripeptide; and (iii) a sugar; and (b) drying the mixture obtained in (a).

All definitions and preferred embodiments described herein with regard to a method for producing stabilised vaccines apply mutatis mutandis to this alternative embodiment for producing stabilised (poly)peptides.

The term "(poly)peptide" in accordance with the present invention describes a group of molecules which comprises the group of peptides, consisting of up to 30 amino acids, as well as the group of polypeptides, consisting of more than 30 amino acids. Also encompassed by the term "(poly)peptide" are proteins as well as fragments of proteins. (Poly)peptides may form dimers, trimers and higher oligomers, i.e. consisting of more than one (poly)peptide molecule. (Poly) peptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "(poly)peptide". The terms "polypeptide" and "protein" are used interchangeably herein. The term "(poly)peptide" also refers to naturally modified (poly)peptides wherein the modification is effected e.g. by post-translational modifications such as e.g. glycosylation, acetylation, phosphorylation and the like. Such modifications are well known in the art.

In a preferred embodiment, the (poly)peptide is selected from the group consisting of therapeutic proteins, like antibodies, growth factors, cytokines, protein or peptide hormones, growth hormones, blood factors, therapeutic enzymes, therapeutic vaccines or fragments thereof which retain their biological activity. These (poly)peptides can be used, for example, for therapeutic or diagnostic purposes. Such purposes are well known in the art.

The term "antibody" includes polyclonal or monoclonal antibodies as well as derivatives thereof which retain their binding specificity. The term also includes synthetic, chimeric, single chain and humanized antibodies or derivatives or fragments thereof, which still retain their binding specificity. Fragments of antibodies comprise, inter alia, Fab fragments, $F(ab')_2$ or Fv fragments. Techniques for the production of antibodies and fragments thereof are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. Further, transgenic animals may be used to express humanized antibodies. Most preferably, the antibody is a monoclonal antibody. For the preparation of monoclonal antibodies, any technique that provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). The antibody may be any class of antibody. It is most preferred that the antibody is monoclonal and of the IgG, IgM or IgY class. IgY antibodies represent the analogs of IgG antibodies in chicken.

The term "growth factor" as used herein refers to proteins that bind to receptors on the cell surface, with the primary result of activating cellular proliferation and/or differentiation. Many growth factors are versatile, stimulating cellular division in numerous different cell types, while others are specific to a particular cell-type. Preferred growth factors in accordance with the present invention include, without being limiting, erythropoietin, insulin-like growth factor 1 (IGF-1, originally called Somatomedin C) and insulin-like growth factor 2 (IGF-2).

The term "cytokine", in accordance with the present invention, relates to a class of signalling proteins that are used extensively in cellular communication, immune function and embryogenesis. Cytokines are produced by a variety of hematopoietic and non-hematopoietic cell types and can exert autocrine, paracrine and endocrine effects as do the hormones. However, many cytokines exhibit growth factor activity. Cytokine are a unique family of growth factors. Secreted primarily from leucocytes, cytokines stimulate both the humoral and cellular immune responses as well as the activation of phagocytic cells. Cytokines that are secreted from lymphocytes are termed lymphokines, whereas those secreted by monocytes or macrophages are termed monokines. A large family of cytokines are produced by various cells of the body. Many of the lymphokines are known as interleukines (ILs), since they are not only secreted by leukocytes but also able to affect the cellular responses of leukocytes. Specifically, interleukines are growth factors targeted to cells of hematopoietic origin. Cytokines include, without being limiting, interleukins, interferons, granulocyte colony-stimulating factor (G-CSF), granulocyte-macrophage colony-stimulating factor (GM-CSF) and bone morphognetic protein-2 (BMP-2).

The term "protein or peptide hormones" refers to a class of peptides that are secreted into the blood stream and have endocrine functions in living animals. Like other proteins, peptide hormones are synthesized in cells from amino acids according to an mRNA template, which is itself synthesized from a DNA template inside the cell nucleus. Peptide hormone precursors (pre-prohormones) are then processed in several stages, typically in the endoplasmic reticulum, including removal of the N-terminal signal sequence and sometimes glycosylation, resulting in prohormones. The prohormones are then packaged into membrane-bound secretory vesicles, which can be secreted from the cell by exocytosis in response to specific stimuli e.g. increase of calcium and cAMP concentration in cytoplasm. These prohormones often contain superfluous amino acid residues that are needed to direct folding of the hormone molecule into its active configuration but have no function once the hormone folds. Specific endopeptidases in the cell cleave the prohormone just before it is released into the bloodstream, generating the mature hormone form of the molecule. Mature peptide hormones then diffuse through the blood to all of the cells of the body, where they interact with specific receptors on the surface of their target cells. Some peptide/protein hormones (angiotensin II, basic fibroblast growth factor-2, parathyroid hormone-related protein) also interact with intracellular receptors located in the cytoplasm or nucleus by an intracrine mechanism. Several important peptide hormones are secreted from the pituitary gland. The anterior pituitary secretes prolactin, which acts on the mammary gland, adrenocorticotrophic hormone (ACTH), which acts on the adrenal cortex to regulate the secretion of glucocorticoids, and growth hormone, which acts on bone, muscle, and the liver. The posterior pituitary gland secretes antidiuretic hormone, also called vasopressin, and oxytocin. Peptide hormones are produced by many different organs and tissues, however, including the heart (atrial-natriuretic peptide (ANP) or atrial natriuretic factor (ANF)) and pancreas (insulin and somatostatin), the gastrointestinal tract cholecystokinin, gastrin), and adipose tissue stores (leptin). Some neurotransmitters are secreted and released in a similar fashion to peptide hormones, and some 'neuropeptides' may be used as neurotransmitters in the nervous system in addition to acting as hormones when released into the blood. When a peptide hormone binds to receptors on the surface of the cell, a second messenger appears in the cytoplasm, which triggers intracellular responses. Peptide hormones include without being limited Insulin, Glucagon, Gonadotropin, human Thyroid Stimulating Hormone, angiotensin II, basic fibroblast growth factor-2, parathyroid hormone-related protein, vasopressin, oxytocin, atrial-natriuretic peptide (ANP) or atrial natriuretic factor (ANF), somatostatin, cholecystokinin, gastrin, and adipose tissue stores (leptin).

The term "growth hormone" (GH) refers to a protein-based peptide hormone consisting of a 191-amino acid, single-chain polypeptide, stored and secreted by somatotroph cells within the lateral wings of the anterior pituitary gland. Effects of growth hormone on the tissues of the body can generally be described as anabolic (building up). Like most other protein hormones, it acts by interacting with a specific receptor on the surface of cells. Increased height during childhood is the most widely known effect of GH. Height appears to be stimulated by at least two mechanisms: 1. because polypeptide hormones are not fat-soluble, they cannot penetrate sarcolemma. Thus, GH exerts some of its effects by binding to receptors on target cells, where it activates the MAPK/ERK pathway. Through this mechanism GH directly stimulates division and multiplication of chondrocytes of cartilage. 2. GH also stimulates, through the JAK-STAT signaling pathway, the production of insulin-like growth factor 1 (IGF-1, formerly known as somatomedin C), a hormone homologous to proinsulin. The liver is a major target organ of GH for this process and is the principal site of IGF-1 production. IGF-1 has growth-stimulating effects on a wide variety of tissues. Additional IGF-1 is generated within target tissues, making it what appears to be both an endocrine and an autocrine/paracrine hormone. IGF-1 also has stimulatory effects on osteoblast and chondrocyte activity to promote bone growth. In addition to increasing height in children and adolescents, growth hormone has many other effects on the body: increases calcium retention, and strengthens and increases the mineralization of bone, increases muscle mass through sarcomere hyperplasia, promotes lipolysis, increases protein synthesis, stimulates the growth of all internal organs excluding the brain, plays a role in homeostasis, reduces liver uptake of glucose, promotes gluconeogenesis in the liver, contributes to the maintenance and function of pancreatic islets, stimulates the immune system.

Somatotropin refers to the growth hormone 1 produced naturally in animals, whereas the term somatropin refers to growth hormone produced by recombinant DNA technology, and is abbreviated "HGH" in humans. It stimulates growth, cell reproduction and regeneration.

The term "blood factors" refers to proteins that govern the functions of the blood coagulation cascade. The coagulation cascade of the human body comprises of a series of complex biochemical reactions, which are regulated by the blood factor proteins. These proteins include, for example, the pro-coagulation factors, such as Factor VIII and Factor IX, as well as anticoagulation factors, including Protein C and Antithrombin III.

As used herein, the term "therapeutic enzymes" refers to proteins that catalyse chemical reactions, thereby converting a starting molecule, the substrate, into a different molecule, the product. The function of therapeutic enzymes depends directly on their molecular structure and conformation. Irreversible conformational changes and irreversible aggregation lead to inactivation of the therapeutic enzymes. Preferred enzymes in accordance with the present invention include, without being limiting, therapeutic enzymes for the treatment of lysosomal storage diseases by enzyme replacement therapy, i.e. human β-glucocerebrosidase (Gaucher disease), human galactosidase A (Fabry disease), thrombolytic drugs, i.e. sreptokinase (thrombolytic agent in treatment of ischemic stroke), urokinase, (recombinant) tissue plasminogen activator, TNKase; L-asparaginase (cytostatic drug), urate oxidase, papain.

A large number of suitable methods exist in the art to produce (poly)peptides. For example, (poly)peptides may be produced in appropriate hosts. If the host is a unicellular organism such as a prokaryote, a mammalian or insect cell, the person skilled in the art can revert to a variety of culture conditions. Conveniently, the produced (poly)peptide is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of (poly)peptides in hosts as indicated above. For example, nucleic acid sequences encoding the (poly)peptide to be folded/prevented from unfolding according to the invention can be synthesized by PCR and inserted into an expression vector. Subsequently a suitable host may be transformed with the expression vector. Thereafter, the host is cultured to produce the desired (poly)peptide(s), which is/are isolated and, optionally, purified before use in the method of the invention.

An alternative method for producing the (poly)peptide to be employed in the method of the invention is in vitro translation of mRNA. Suitable cell-free expression systems include rabbit reticulocyte lysate, wheat germ extract, canine pancreatic microsomal membranes, *E. coli* S30 extract, and coupled transcription/translation systems such as the TNT-system (Promega). These systems allow the expression of recombinant (poly)peptides upon the addition of cloning vectors, DNA fragments, or RNA sequences containing coding regions and appropriate promoter elements.

In addition to recombinant production, the (poly)peptide to be employed in the method of the invention may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic peptide synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used. Furthermore, the (poly)peptide may be produced semi-synthetically, for example by a combination of recombinant and synthetic production.

(Poly)peptide isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis.

In a preferred embodiment of the method of the invention, the at least three amino acids are selected from the groups of (a) amino acids with non polar, aliphatic R groups; (b) amino acids with polar, uncharged R groups; (c) amino acids with positively charged R groups; (d) amino acids with negatively charged R groups; and (e) amino acids with aromatic R groups.

The naturally occurring amino acids, but also other than naturally occurring amino acids such as artificial amino acids, can be classified into the above characteristic groups (Nelson D. L. & Cox M. M., "Lehninger Biochemie" (2005), pp. 122-127), from which at least three amino acids are selected for the solution according to the invention.

In a more preferred embodiment, the at least three amino acids are selected from different groups (a) to (e). In other words, in this preferred embodiment, when three amino acids are comprised in the solution, the three amino acids may be selected from at least two different groups and, more preferably, from three different groups such that for example one is from group (a), one is from group (b) and one is from group (c). Further combinations such as e.g. (b)-(c)-(d), (c)-(d)-(e), (e)-(a)-(b), (b)-(d)-(e) and so forth are also explicitly envisaged herein. The same consideration applies when four amino acids are comprised in the solution, in which case the amino acids have to be from at least two different groups selected from (a) to (e), more preferably from at least three different groups and most preferably from four different groups. Inter alia, when five amino acids are comprised in the solution, the amino acids have to be from at least two different groups selected from (a) to (e), more preferably from at least three different groups, more preferably from at least four different groups and most preferably from five different groups. The same considerations apply when more than five amino acids are comprised in the solution, such as e.g. six or seven amino acids, in which case these amino acids are selected from at least two different groups selected from (a) to (e), more preferably from at least three different groups, even more preferably from at least four different groups and most preferably from all five different groups.

In a more preferred embodiment of the method of the invention, the solution comprises at least one amino acid selected from each group of (a) an amino acid with non polar, aliphatic R groups; (b) an amino acid with polar, uncharged R groups; (c) an amino acid with positively charged R groups; (d) an amino acid with negatively charged R groups; (e) an amino acid with aromatic R groups.

The skilled person further understands that it is not necessary that the same number of amino acids of each group is present in the solution used according to the invention. Rather, any combination of amino acids can be chosen as long as at least one amino acids of each group is present.

In another preferred embodiment of the method of the invention, the solution comprises at least the amino acids: (a) alanine, glutamate, lysine, threonine and tryptophane; (b) aspartate, arginine, phenylalanine, serine and valine; (c) proline, serine, asparagine, aspartate, threonine, phenylalanine; (d) tyrosine, isoleucine, leucine, threonine, valine; (e) arginine, glycine, histidin, alanine, glutamate, lysine, tryptophane, or (f) alanine, arginine, glycine, glutamate, lysine.

In accordance with this embodiment, at least the above recited amino acids of either group (a), (b), (c), (d), (e) or (f) are present in the solution in accordance with the invention. In other words, whereas more than the above recited amino acids may be comprised in the inventive solution, it is required that at least the recited amino acids are present. More preferably, the solution comprises exactly the recited amino acids and no other amino acids.

In a further preferred embodiment of the method of the invention, one or more of the amino acids are selected from the group consisting of natural non-proteinogenic amino acids and synthetic amino acids.

The term "non-proteinogenic amino acids", in accordance with the present invention, relates to amino acids that are not naturally incorporated into polypeptides and proteins. Non-proteinogenic amino acids can be derived from proteinogenic amino acids, which are L-α-amino acids, by post-translational modifications. Such non-proteinogenic amino acids are, for example, lanthionine, 2-aminoisobutyric acid, dehydroalanine, and the neurotransmitter gamma-aminobutyric acid. Also the D-enantiomers of proteinogenic L-amino acids represent non-proteinogenic amino acids. Further non-limiting examples of non-proteinogenic amino acids include carnitine, creatine, creatinine, guanidinoacetic acid, ornithine, hydroxyproline, homocysteine, citrulline, hydroxylysine or beta-alanine.

The term "synthetic amino acids", as used herein, relates to amino acids not naturally occurring in nature. Non-limiting examples of synthetic amino acids include (2R)-amino-5-phosphonovaleric acid, D-phenyl glycine or (S)- and (R)-tert-leucine.

In another preferred embodiment of the method of the invention, the at least one of the dipeptide(s) is selected from the group consisting of carnosin, glycyltryrosine, glycylglycine and glycylglutamine.

For the most injectable pharmaceutical formulations a physiological osmolality of approximately 300 mOsmol/kg is required. An osmolality of approximately 400 mOsmol/lkg is widely accepted. But the Osmolality of a mixture of e.g. 10 components (amino acids) achieves a significant greater Osmolality. In the most stabilizing applications the side chains are the reactive part of the molecule associated with their protective efficacy. Hence the application of dipeptides containing the same side chains can reduce the osmolality of the formulation. Furthermore, the reactivity of some functional groups may be reduced in the dipeptide.

In another preferred embodiment of the method of the invention, the sugar is trehalose.

Trehalose is a natural α-linked disaccharide formed by an α,α-1,1-glucoside bond between two α-glucose units. It is also known as mycose or tremalose. Trehalose is well known in the art and can be obtained commercially, for example from Sigma-Aldrich, as shown in the appended examples.

Preferred amounts of trehalose to be employed are as described herein above with regard to the amounts of sugar to be employed.

In another preferred embodiment of the method of the invention, the solution further comprises at least one saponine.

Saponines are a class of chemical compounds forming secondary metabolites which are found in natural sources, derived from natural sources or can be chemically synthesised. Saponines are found in particular abundance in various plant species. Saponines are amphipathic glycosides grouped phenomenologically by the soap-like foaming they produce when shaken in aqueous solutions, and structurally by their composition of one or more hydrophilic glycoside moieties combined with a lipophilic steroidal or triterpenoid aglycone. Their structural diversity is reflected in their physicochemical and biological properties. Non-limiting examples of saponines are glycyrrhizic acid, glycyrrhetinic acid, glucuronic acid, escin, hederacoside and digitonin.

Preferably, the saponine is glycyrrhizic acid or a derivative thereof. Glycyrrhizic acid is also known as glycyrrhicic acid, glycyrrhizin or glycyrrhizinic acid. Glycyrrhizic acid is water-soluble and exists as an anion that can be a potential ligand to form electrostatically associated complexes with cationic molecules of active ingredients. Without wishing to be bound by theory, the present inventors hypothesise that the anionic glycyrrhizic acid forms complexes with amino acids present in the solution of the present invention (i.e. arginine, or lysine) through electrostatic interactions, hydrogen bonds or both. This complex-formation is thought to enhance the ability of the solution of the present invention to stabilise the vaccine during drying and storage. Moreover, the ability of glycyrrhizic acid to form complexes with cationic molecules of active ingredients can lead to stabilising interactions with exposed cationic side chains on the protein surface during the storage process.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-D-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e.g. in Kondratenko et al. (Russian Journal of Bioorganic Chemistry, Vol 30(2), (2004), pp. 148-153).

Preferred amounts of glycyrrhizic acid (or derivatives thereof) to be employed are between 0.01 and 15 mg/ml, preferably between 0.1 and 10 mg/ml, more preferably between 0.5 and 5 mg/ml, even more preferably between 1 and 3 mg/ml and most preferably the amount is 2 mg/ml.

As is known in the art, saponines, in particular glycyrrhizic acid, has been found to be advantageously present in stabilising formulations, as it enhances the stabilising effect of other excipients.

In a further preferred embodiment of the method of the invention, the antigens are selected from the group consisting of influenza subunit antigen, hemagglutinin, neuraminidase, cholera toxin B subunit, hepatitis B surface antigen, toxoids, HIV envelope protein, anthrax recombinant protective antigen, other pathogen surface proteins and virus envelope components In a more preferred embodiment of the method of the invention, the antigens are split virus antigens.

Split-virus antigens are well known in the art and are commonly employed as a basis for vaccines (WHO, Unicef, WorldBank. State of the world's vaccines and immunization. 3rd ed. Geneva: World Health Organisation, 2009.). Split-virus antigens are obtained by inactivating and disrupting a virus by e.g. a detergent or by other techniques, without further removal of other viral components. Split-virus vaccines are often employed for vaccination against, amongst other, influenza, hepatitis A, Japanese encephalitis, poliomyelitis or rabies. It is even more preferred that the split virus antigens are influenza virus antigens. Influenza virus is part of the family of Orthomyxoviridae and belongs to virus group V ((−)ssRNA). The three genera of influenza virus known—influenza virus A, B and C—are identified by antigenic differences in their nucleoprotein and matrix protein. Influenzavirus A infects humans, other mammals, and birds, and causes flu pandemics; influenzavirus B infects humans and seals and influenzavirus C infects humans and pigs.

The main antigenic structures of influenza split vaccines are the integral membrane glycoproteins hemagglutinin (HA) and neuraminidase (NA) [3, 26]. Together with other proteins, including matrix proteins (MP1; MP2) and nucleoprotein (NP) and several minor components from the membrane lipid matrix, they form the constituents of the split vaccine.

The preparation of stable split-virus influenza vaccines is typically difficult, as the 3-dimensional structure of hemagglutinin contains highly hydrophobic regions that make it susceptible to form soluble aggregates and protein complexes with other influenza constituents [26]. In addition, hemagglutinin is susceptible to freezing stresses, particularly sensitive to pH drops and to changes in the concentration of solutes during freezing, leading to irreversible conformational changes and denaturation, while elevated temperatures can cause inactivation of the virus antigen [3]. In addition, the problem of terminal sterilisation has not been resolved successfully so far.

In the past decades, several papers have been published in which dried influenza vaccines were used. However, the development of dry-state influenza vaccines is still in a very early stage. Incorporation of influenza vaccines in amorphous glassy carbohydrate matrices can stabilize the various antigens against different kinds of stresses associated with different drying methods. However, for each drying method and for each influenza antigen the stability of the vaccine was dependent on the type of the chosen carbohydrate glassy matrix. Each vaccine type may possess its own intrinsic sensitivity to different stresses associated with the different drying methods. Many aspects of stabilization of influenza vaccines, in particular the comparison of the different drying methods for the production of stabilized influenza vaccines, had to be further investigated. As a result, the incorporation of a vaccine compound in carbohydrate glasses needs be optimized by both formulation and drying process considerations. Additional data on long term stability of dry influenza vaccine formulations and pre- and clinical studies are very limited. In the dry state, the long-term stability of the influenza vaccines is still very limited, especially at elevated temperatures. It was shown that the storage stability of dried influenza vaccines was dependent on the type of carbohydrate, the type of buffer and storage conditions. Terminal sterilization is up to date not considered to be a part of the production process of influenza vaccine antigens [3].

In accordance with the present invention, these problems could successfully be addressed by the method of the invention, thereby preparing a highly stable split-virus influenza vaccine powder, as shown in the appended examples. As is evident from those data, incorporation in a sugar matrix alone was not sufficient to stabilise the vaccine during spray drying or freeze drying followed by terminal sterilisation. Further, thermal stabilisation could not be achieved with the liquid preparation nor with a dried preparation without stabilisation using the solution of the invention.

More preferably, the influenza virus is influenza A virus and most preferably, the influenza virus is influenza A H1N1 virus. Even more preferably, the influenza A H1N1 virus is the inactivated, split virion A/California/7/2009 (H1N1)v like strain (x-179a).

In another preferred embodiment of the method of the invention, the w/w ratio between the excipients of the solution and the antigen is between about 1:1 and about 30.000:1.

In accordance with this embodiment, the excipients of the solution are the non-aqueous components of the solution that are not the antigen to be stabilised.

More preferably, the w/w ratio between the components of the solution and the antigen is between about 1:1 and about 25.000:1, such as for example between about 5:1 and about 20.000:1. Most preferably, the w/w ratio is about 16.267:1. It will be understood that any value falling between these ratios is explicitly also envisaged herein. Furthermore, the term about, as used herein, encompasses the explicitly recited ratios as well as deviations therefrom of ±10%.

In a further preferred embodiment of the method of the invention, the step of drying the mixture is achieved by a method selected from the group consisting of spray drying, lyophilisation, spray-freeze drying, supercritical drying and air or vacuum drying.

Spray-drying is well known in the art and is a method to convert a solution, suspension or emulsion into a solid powder in one single process step. Generally, a concentrate of the liquid product is pumped to the atomising device, where it is broken into small droplets. These droplets meet a stream of hot air and they lose their moisture very rapidly while still dispersed in the drying air. The dry powder is separated from the moist air in cyclones by centrifugal action, the dense powder particles are forced toward the cyclone walls while the lighter, moist air is directed away through the exhaust pipes.

Lyophilisation, also referred to as freeze-drying, is also well known in the art and includes the steps of freezing the sample and subsequently reducing the surrounding pressure while adding sufficient heat to allow the frozen water in the material to sublime directly from the solid phase to the gas phase followed by a secondary drying phase. Preferably, the lyophilised preparation is then sealed to prevent the re-absorption of moisture.

Spray-freeze-drying is also well known in the art and is a method that combines processing steps common to freeze-drying and spray-drying. The sample provide is nebulised into a cryogenic medium (such as e.g. liquid nitrogen), which generates a dispersion of shock-frozen droplets. This dispersion is then dried in a lyophiliser.

Supercritical drying is another technique well known in the art. This method relies on high-temperature and high-pressure above the critical temperature ($T_c$) and critical pressure ($p_c$) to change a liquid into a gas wherein no phase boundaries are crossed but the liquid to gas transition instead passes through the supercritical region, where the distinction between gas and liquid ceases to apply. The densities of the liquid phase and vapor phase become equal at the critical point of drying.

Air drying refers to drying the sample by exposing it to the surrounding air, optionally combined with moderate heating of the sample, ventilation of the air or evacuation of the drying chamber (vacuum drying).

In a further preferred embodiment of the method of the invention, the dried vaccine obtained in step (b) is subsequently sterilised. Preferably, the vaccine is packed in single or multiple dose containers prior to said terminal sterilisation step.

The term "sterilising" refers to a process wherein all live organisms are killed. Methods of sterilisation are well known in the art and include, for example, sterilisation by beta irradiation, by gamma irradiation thermal sterilisation, gas sterilisation, sterilisation by ethylene oxide (EO) as well as plasma sterilisation. Preferably, the sterilisation is effected by gamma- or beta-irradiation.

Preferably, the thus obtained sterile vaccine powder is subsequently stored under sealed conditions, such as e.g. in a sealed container or vial, until its use.

As shown in the appended examples, the antigenicity of the antigens present in a vaccine powder produced in accordance with the method of this invention is maintained after sterilisation. Thus, the method of the present invention provides a vaccine preparation method that enables the preparation of stable and safe antigens, wherein the antigens are stabilised in the solution according to the invention, thereby maintaining their naturally occurring three-dimensional appearance.

In a further preferred embodiment of the method of the invention, the vaccine is for intramuscular, subcutaneous, intradermal, transdermal, oral, peroral, nasal, and/or inhalative application.

The present invention further relates to vaccine comprising (an) antigen(s), chitosan, at least three different amino acids and/or at least one dipeptide or tripeptide, and a sugar. This vaccine has an improved stabilisation during storage and sterilisation. Preferably, the stabilised vaccine of the invention is a vaccine obtained or obtainable by the method of producing a stabilised vaccine of the present invention. All of the definitions and preferred embodiments with regard to the method of producing a stabilised vaccine of the present invention apply mutatis mutandis also to the stabilised vaccine of the present invention.

The present invention further relates to a (poly)peptide composition, comprising (a) (poly)peptide(s), chitosan, at least three different amino acids and/or at least one dipeptide or tripeptide, and a sugar. This (poly)peptide composition has an improved stabilisation during storage and sterilisation. Preferably, the stabilised (poly)peptide composition of the invention is a (poly)peptide composition obtained or obtainable by the method of producing a stabilised (poly)peptide of the present invention. All of the definitions and preferred embodiments with regard to the method of producing a stabilised (poly)peptide of the present invention apply mutatis mutandis also to the stabilised (poly)peptide composition of the present invention.

As regards the embodiments characterised in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 12, 7 and any one of claims 4(a) to 4(f) is clearly and unambiguously envisaged in view of the claim structure. The same applies for example to the combination of claims 12, 8, 7 and any one of claims 4(a) to 4(f), etc.

Unless otherwise defined, all technical and scientific terms used herein have the same meaning as commonly understood by one of ordinary skill in the art to which this invention belongs. In case of conflict, the patent specification, including definitions, will prevail.

The figures show:

FIG. 1: Differential Scanning Fluorimetry

Normalized thermal denaturation curves of the model protein in combination with different stabilizing excipients alone or excipient mixtures compared to the corresponding thermal denaturation profile of the model protein in PBS buffer. Thermal denaturation curves of the model protein in different concentrations of trehalose (A), chitosan (B), SPS (C), SPS+trehalose (D), SPS+chitosan (E) and SPS+trehalose+chitosan (F), Comparison of the normalized thermal denaturation curves of the analysed model protein for all excipients and excipient mixture in a selected concentration range (G).

Figure 2:
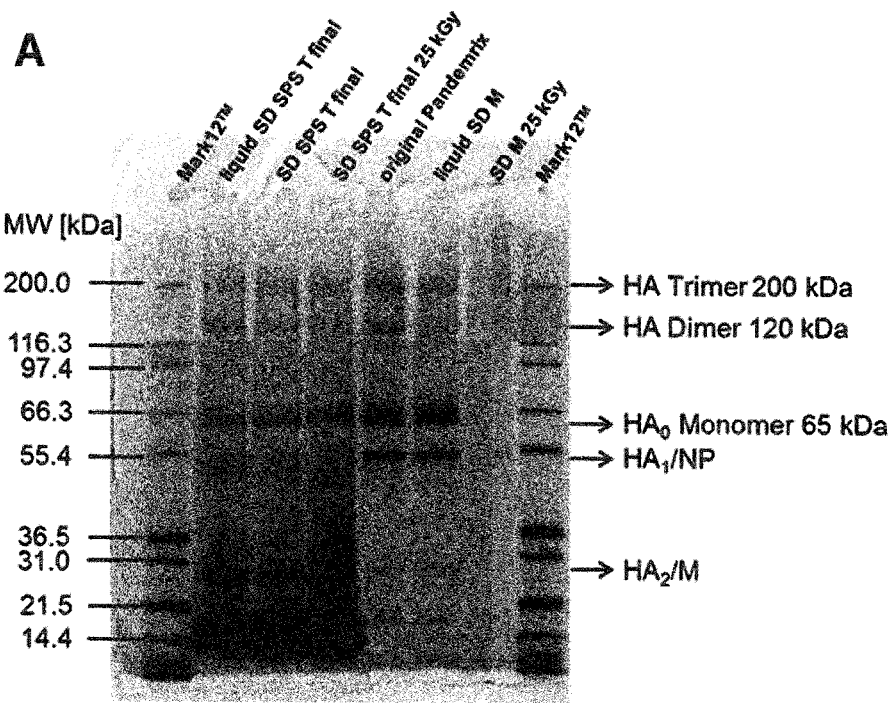
Figure 2:
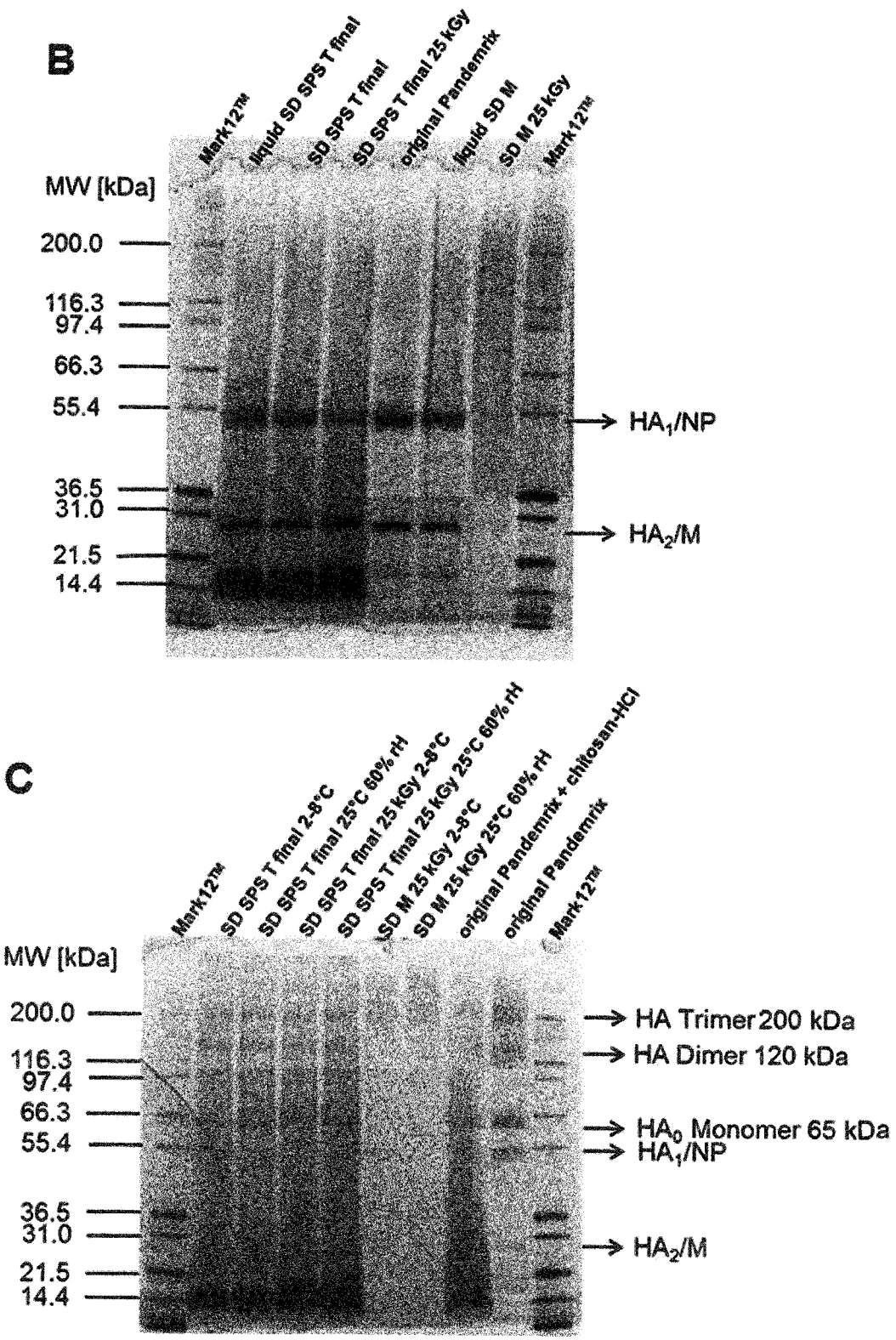
Figure 2:
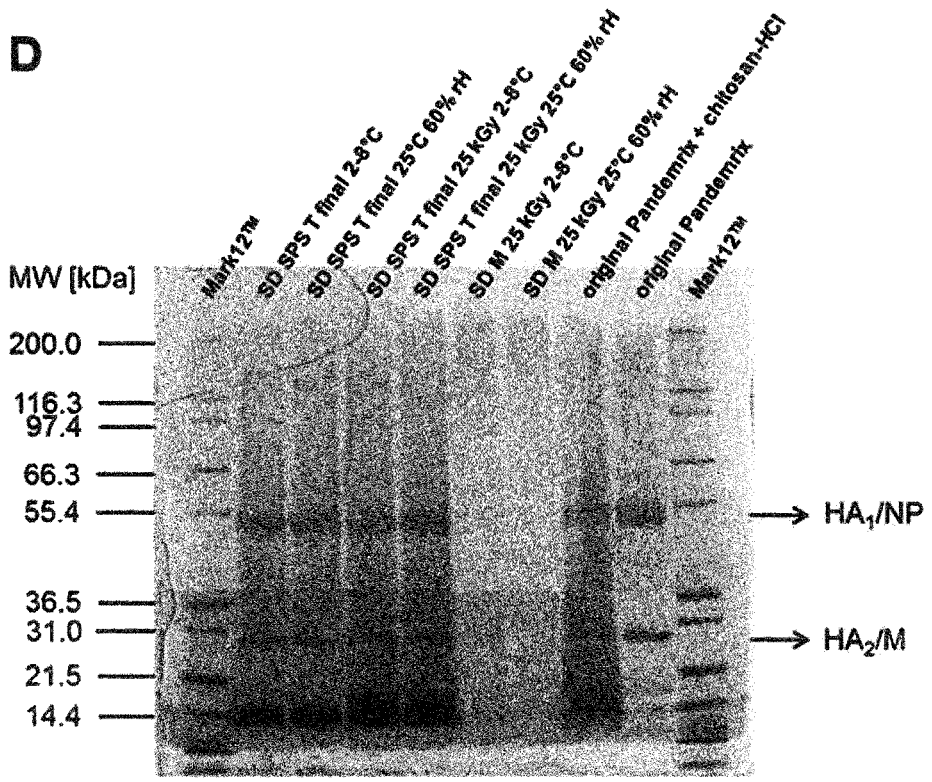
Figure 2:
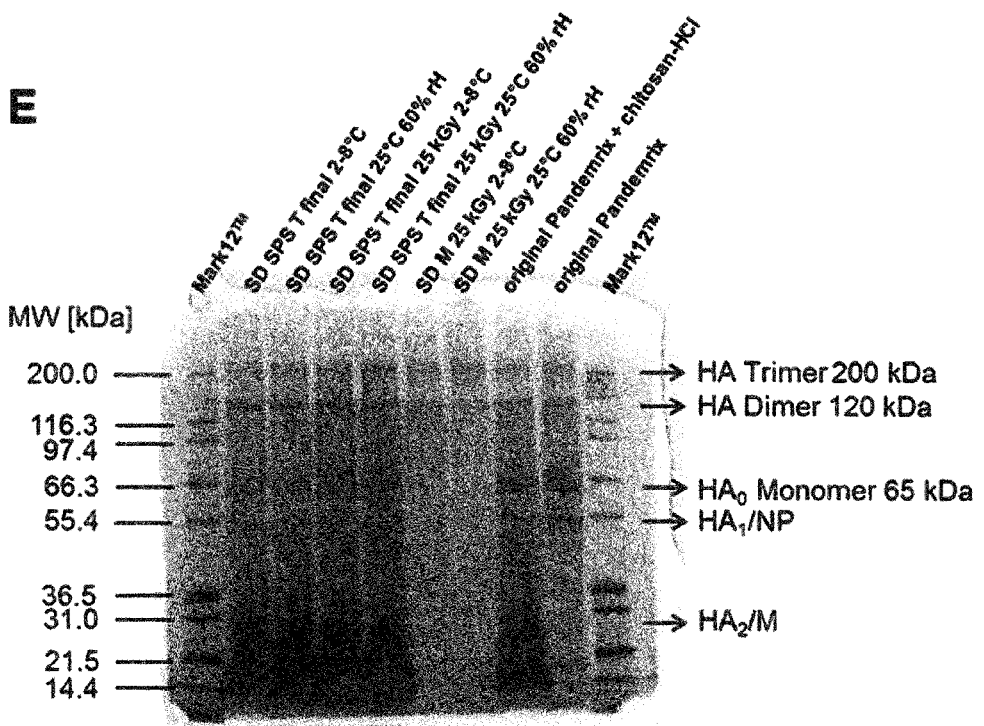
Figure 2:
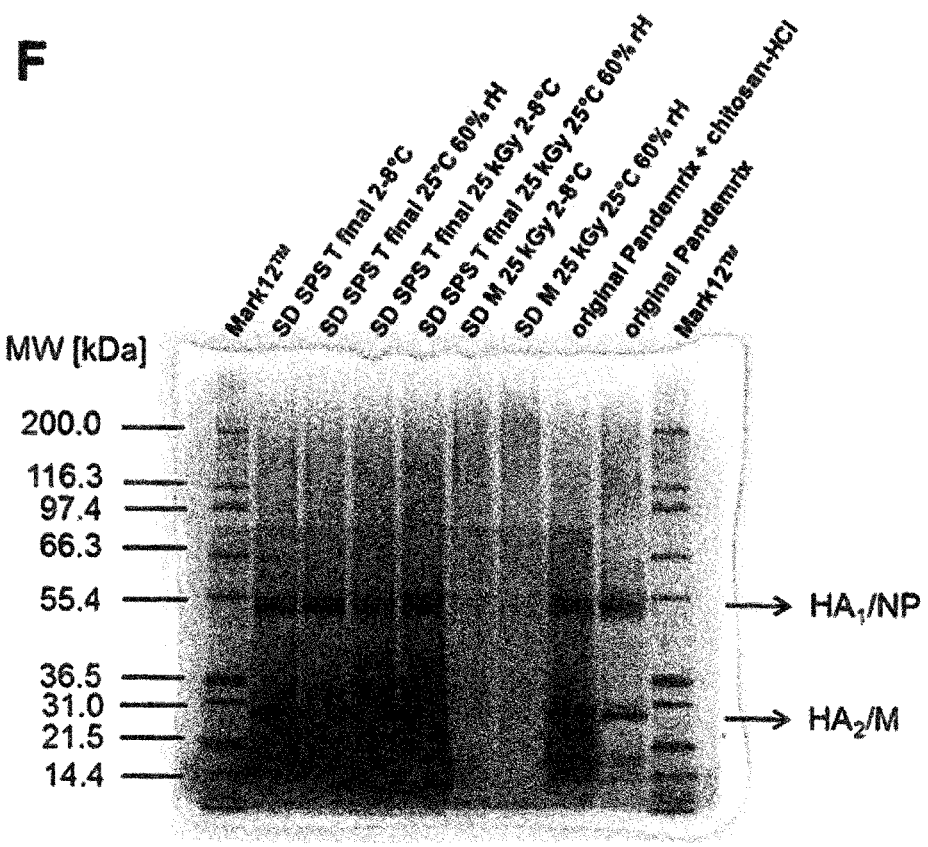

FIG. 2: SDS-PAGE monitoring of the selected variants over time.

Non-reducing SDS-PAGE (A) and reducing SDS-PAGE (B) of the different formulations of the influenza vaccine before and after spray-drying and subsequent irradiation at 25 kGy (e-beam) at the time point t=0. The samples are loaded for each treatment condition in the following order: Mark12 (lane 1); liquid SPS T final prior to SD (lane 2); SD SPS Trehalose final (lane 3); SD SPS T final 25 kGy (lane 4); original Pandemrix (positive control; lane 5); liquid M prior to SD (lane 6); SD M 25 kGy (lane 7); Mark12 (lane 8). Non-reducing SDS-PAGE (C and E) and reducing SDS-PAGE (D and F) of the different formulations of the influenza vaccine before and after spray-drying and subsequent irradiation at 25 kGy (e-beam) at the time point t=1 month (C, D) and t=3 months (E, F). The samples are loaded for each treatment condition in the following order: Mark12 (lane 1); SD SPS T final 2-8° C. (lane 2); SD SPS T final 25° C. 60% rH (lane 3); SD SPS T final 25 kGy 2-8° C. (lane 4); SD SPS T final 25 kGy 25° C. 60% rH (lane 5); SD M 25 kGy 2-8° C. (lane 6); SD M 25 kGy 25° C. 60% rH (lane 7); original Pandemrix+chitosan-HCl (lane 8); original Pandemrix (positive control; lane 9); Mark12 (lane 10).

FIG. 3: Immune responses in macaques to Pandemrix vaccine. A, Haemagglutination inhibition assay (HAI) titre; B, Microneutralisation assay (MN) titre. In each chart, bars represent the geometric mean titre for each group. Group 1: negative control group (PBS); Group 2: original Pandemrix; Group 3: SD M 25 kGy; Group 4: SD SPS T final; Group 5: SD SPS T final 25 kGy. *, significant difference from group 2, 4 and 5 means, $p<0.01$. Means for groups 2, 4 and 5 are not significantly different from one another at any timepoint.

FIG. 4: Dynamic light scattering. Particle size distribution by dynamic light scattering of A) original Pandemrix; SD M; SD M 25 kGy; SD SPS T final; SD SPS T final 25 kGy B) SD M 25 kGy, prepared freshly and after 1 and 3 month storage at 2-8° C. and 25° C., 60% rH C) SD SPS T final; prepared freshly and after 1 and 3 month storage at 2-8° C. and 25° C., 60% rH D) SD SPS T final 25 kGy, prepared freshly and after 1 and 3 month storage at 2-8° C. and 25° C., 60% rH FIG. 5: SEC-Analyses. SEC chromatograms of A) original Pandemrix; SD M; SD M 25 kGy; SD SPS T final; SD SPS T final 25 kGy B) SD M 25 kGy, prepared freshly and after 1 and 3 month storage at 2-8° C. and 25° C., 60% rH C) SD SPS T final; prepared freshly and after 1 and 3 month storage at 2-8° C. and 25° C., 60% rH D) SD SPS T final 25 kGy, prepared freshly and after 1 and 3 month storage at 2-8° C. and 25° C., 60% rH.

FIG. 6: Water content in % of different formulations after spray drying as determined by Karl-Fischer titration. Results are shown as mean±SD values (n=3).

FIG. 7: LDH enzyme activities normalized in % of a standard activity in 4 SPS variants upon liquid storage at a temperature of 50° C. before storage t=0 days and after 2 days, 4 days, 7 days and 14 days in comparison to the storage of LDH in 100 mM sodium phosphate buffer. The measured LDH activity was normalized to a standard curve.

FIG. 8: Comparison of the specific LDH enzyme activity before (t=0 days) and after liquid storage at the indicated time points (t=14; 16; 18 and 21 days) formulated with either trehalose and chitosan (left side of the figure) or with a mixture of 7 amino acids, trehalose and chitosan (right side of the figure).

FIG. 9: LDH enzyme activities normalized in % of a standard activity before (t=0) and after liquid storage of LDH formulated with the main components employed in WO 2009/014774 (Pluronic F127 and rHSA) as compared to a combination of 7 amino acids, trehalose and chitosan with these components at 50° C. measured at the indicated time points (t=2; 4 and 7 days).

The examples illustrate the invention.

EXAMPLE 1: MATERIALS AND METHODS

Stabilizing and Protecting Solution (SPS)

The proprietary aqueous Stabilizing and Protecting Solution (SPS; LEUKOCARE, Munich, Germany) is composed of different small molecules (here mostly amino acids) and glycosidic excipients (here, glycyrrhizinic acid) usually provided as a stock concentration of 80 mg/mL (pH 7). All components are used in pharmaceutical quality; they are non-toxic and routinely used in parenteral solutions.

Influenza Strain

Pandemrix (Glaxo Smith Kline) was used as the antigen vaccine. Pandemrix is provided in two vials, one of which contains an influenza (split virion, inactivated) A/California/7/2009 (H1N1)v like strain (x-179a) that comprises the main antigen hemagglutinin. The second vial comprises the adjuvant, AS03 (squalene (10.69 mg per dose), DL-α-tocopherol (11.86 mg) and polysorbate 80 (4.86 mg)). 15 µg/ml of the antigen dispersion (are usually mixed 1:1 with adjuvant prior to injection (3.74 µg HA per dose 500 µl). For the present study, the split viral antigens of the first vial were re-formulated as described, dried and sterilised. Prior to injection, said re-formulated antigen preparations were resuspended and mixed 1:1 with adjuvant, as described above.

Differential Scanning Fluorimetry

SYPRO orange (5000× stock solution; Life Technologies (Carlsbad, Calif.) was diluted 1:1000 in different concentrations of the stabilizing excipient mixtures or in PBS buffer to a 5× final concentration. In the next step the model protein was diluted to 300 µg/ml and 600 µg/ml, respectively with the 5×SYPRO orange solutions of these different concentrations of the stabilizing excipients or with buffer and subsequently distributed as 50 µl aliquots into the wells of a 96-well PCR plate (4titude, Berlin). The PCR plates were sealed with a PCR film (4titude, Berlin) and 1 min centrifuged at 500 g at room temperature to avoid creating air bubbles and to collect the solution at the bottom of the wells. The plates were subsequently heated on a q-PCR Light-Cycler 480 II (Roche) from 20 to 95° C., with a ramping rate of 3° C. min$^{-1}$. The set up of the filter configuration was the optimal excitation wavelength of 498 nm and emission wavelength of 610 nm for SYPRO orange. The midpoint of thermal denaturation $T_m$ was calculated by fitting the data to the Boltzmann equation using GraphPad Prism 6. The differences in $T_m$ between the control samples of the model protein in PBS and the stabilizing excipients containing formulations were calculated as thermal shift.

Formulation Variants

For in vitro testing, a range of formulation variants were spray dried of which a small number was selected for the in vivo study. A summary of the formulation variants and names used throughout the present application are given in Table 3. Original Pandemrix was either used as supplied and mixed with the matrix component in the respective amount or in case of the SPS containing formulations it was dialysed overnight against SPS in the respective concentrations at pH 7, using Slide-A-Lyzer® dialysis cassettes (cut-off 3.5 kDa; volume 3-12 mL) (Thermo Scientific, Schwerte-Geisecke, Germany). The additional components mannitol, trehalose and glycyrrhizinic acid (Sigma-Aldrich, Munich, Germany), respectively, were added afterwards. For in vivo batches, chitosan-HCl was also added (Heppe Medical Chitosan GmbH, Halle a. d. Saale, Germany).

Spray-Drying

A Büchi B-290 laboratory spray-dryer (Büchi, Flawil, Switzerland) was used for spray-drying of the vaccine preparations (see table 4 for parameters). The dried product was collected in the product vessel using a high performance cyclone, sealed in glass vials and was stored at 2 to 8° C. until analysis. For the batches of the in vivo study, all components of the spray-dryer were disinfected with 70% (V/V) isopropanol prior to use. Dried products were filled in individual doses in pre-sterilised glass vials (Type I, 2R, PRI-PAC e.K. Eschweiler, Germany) under aseptic conditions.

Haemagglutination Assay

Dried samples were reconstituted in water (15 μg HA/mL). To determine HA titres, 50 μL of the diluted split vaccine formulations were two-fold serially diluted in 50 μL PBS mixed with an equal volume of fresh 0.5% (W/V) chicken red blood cell suspension (Harlan Laboratories, Belton, Leicestershire, UK) in a U-bottom 96 well microtitre plate. After one hour incubation at room temperature, the plates were scored for agglutination. The titres are given as inverse of the highest dilution causing the agglutination of red blood cells.

Electrophoresis

Spray dried products were reconstituted in water (15 μg HA/mL). For denaturing conditions, the samples were prepared by mixing 12 μL of the vaccine formulation with 12 μL of the NuPAGE LDS-sample buffer 2× concentrate (Invitrogen, Darmstadt, Germany). Separation was performed at a constant voltage of 200 V and running time was ~90 min. Gels were stained with a silver staining kit (SilverXpress silver staining kit, Invitrogen). A molecular weight standard (Novex Mark 12™ Unstained Standard, Invitrogen) was analysed on each gel.

Irradiation Protocol

Sterilisation of the spray dried and freeze dried vaccine samples was performed in sealed glass vials by BGS, Saal a. d. Donau, Germany, using β-irradiation at 25 or 40 kGy. Samples for the in vivo study and long term storage were β-irradiated with 25 kGy.

Long Term Storage

For the formulations chosen for the in vivo study, extensive characterisation directly after production and over storage was performed. All formulations were packed in glass vials, were sealed and stored at 2 to 8° C., or at 25° C. (+/−2° C.) at 60% (+/−5%) relative humidity (rH), respectively. After one month and after three months, samples were analysed. Characterisation included hemagglutination assay, DLS measurements, water content, SEC profiling and electrophoresis.

Size Exclusion Chromatography (SEC)

Size exclusion chromatography (SEC) was performed by using an Merck-Hitachi D 7000 system (Merck-Hitachi, Darmstadt, Germany) with UV detector at 214 nm and a 13 μm TSKgel GMPWXL SEC column (7.8×300 mm) (TOSOH Bioscience GmbH, Stuttgart, Germany). Samples were run in a mobile phase of PBS pH 7.4 (flow rate 0.7 mL/min). A sample amount equivalent to 15 μg HA was used for each analysis. All measurements were performed in duplicates.

Dynamic Light Scattering (DLS)

Dynamic Light Scattering was performed to analyse for protein aggregates using a Malvern Zetasizer Nano-ZS (Malvern Instruments, Worcestershire, UK). A sample amount equivalent to 15 μg of protein (HA) was redispersed in double distilled water and was measured. All results are mean of three sets of 30 individual scans.

Water Content 50 mg of the spray dried product was dissolved in 1 mL of dimethylsulfoxide (DMSO) and added to the titration flask of the Karl Fischer titrator (V20, Mettler Toledo AG, Schwerzenbach, Switzerland). Titration was then carried out using Karl Fischer reagent of previously determined titre (mg $H_2O$/mL). Water content was determined in triplicate for each sample and was subtracted for solvent. Results are shown as mean±SD values.

Animal Study

The study was approved by the Ethical Review Process of Public Health England, Porton, Salisbury, UK and the Home Office via Project License PPL30/2993. The study was conducted in accordance with the PHE Porton Down Quality Management System that is compliant with BS EN ISO9001-2000.

Animals (*Macaca fascicularis*) consisted of mature adults with equal distribution of male and female animals in each group. Twenty-six mature adult animals of either sex (age range 4 to 6 years and weight range 3.6 to 5.9 kg at the start of the study) were obtained from a Home Office accredited breeding colony within the United Kingdom. All animals were maintained within a conventional colony tested to be free of *Herpesvirus simiae* (B-virus), *Mycobacterium tuberculosis* (TB), Simian T-cell Lymphotropic virus (STLV) and Simian immunodeficiency virus (SIV) and were selected from a cohort of animals screened for the absence of influenza antibodies.

The animals were housed in their existing social groups in pens designed in accordance with the requirements of the United Kingdom Home Office Code of Practice for the Housing and Care of Animals Used on Scientific Procedures (1989). Each animal was individually identified by a permanent tattoo using a unique number. Tap water and Expanded Primate Maintenance diet (PME, Special Diet Services, UK) were available ad libitum with enrichment treats, vegetables and fruit provided on a regular basis.

| Animal Groups: | | |
|---|---|---|
| Group 1: | Negative control (PBS) | 2 animals |
| Group 2: | Original Pandemrix | 6 animals |
| Group 3: | SD M 25 kGy | 6 animals |
| Group 4: | SD SPS T final | 6 animals |
| Group 5: | SD SPS T final 25 kGy | 6 animals |

Original Pandemrix consisted of the human vaccine formulation, including the AS03 adjuvant provided as a separate flask. The spray dried products were supplied in single dose vials and were reconstituted with sterile water and AS03 adjuvant immediately prior to vaccination. Each animal was given 0.5 ml vaccine preparation containing 3.75 μg HA antigen (human adult dose). All vaccinations were given by intramuscular injection. Control sera were taken eight days prior to vaccination, and sera were taken at 21, 34 and 48 days post-vaccination. A booster immunisation was given 28 days post-vaccination, with an equal dose of the appropriately-treated vaccine. At every sampling or vaccination occasion each animal was weighed, had a rectal temperature taken, superficial lymph nodes (inguinal and axillary) palpated, the site of vaccination examined and a check was made of general physical condition. In addition, haemoglobin levels were checked at each blood sampling occasion.

Haemagglutination Inhibition Assay (HAI)

Sera were treated with receptor-destroying enzyme (RDE, Denka Seiken Co., Japan), followed by heat-inactivation. Treated sera were then subjected to 2-fold serial dilutions in 96-well U-bottom plates, followed by the addition of 4 HA units of virus (influenza A/California/07/09). After incubating at room temperature, a 0.5% w/v suspension of chicken red blood cells was added as described above for the HA assay. The end-point was defined as the highest serum dilution showing complete HA inactivating activity.

Microneutralisation Assay (MN)

RDE-treated sera were subjected to 2-fold serial dilutions in 96-well cell culture plates. The diluted sera were mixed with an equal volume of medium containing 100 TCID50 influenza A/California/07/09 virus. After incubation, 100 µl of Madin-Darby canine kidney (MDCK) cells were added to each well. The plates were incubated for 18 to 20 hours. Cell monolayers were washed with PBS and fixed. Presence of viral antigen was detected with a primary antibody to the influenza A NP protein followed by a secondary peroxidase conjugate. After staining, absorbance was read at 492 nm. The reciprocal serum dilution corresponding to the lowest dilution to be scored negative for neutralising activity is the 50% neutralisation antibody titre.

Data Analysis.

Data from animal study are depicted as geometric mean values of n=6 animals per group. Minitab 15 software was used to conduct nonparametric analyses using Mann-Whitney Rank Sum Test. Intergroup differences were considered significant at $p<0.01$.

EXAMPLE 2: DIFFERENTIAL SCANNING FLUORIMETRY (DSF)—THERMAL SHIFT ASSAY

Thermal profiles of a model protein were monitored in the presence of an environmentally sensitive fluorescent dye which is highly fluorescent in non-polar environment, such as the hydrophobic sites of unfolded proteins, compared to the aqueous solution where the fluorescence is quenched. The temperature at which a protein unfolds is measured by an increase in the fluorescence of the applied dye with affinity to hydrophobic parts of the protein, which are exposed as the protein unfolds. The plot of the fluorescence intensity as a function of temperature generated a sigmoidal curve that can be described by a two state transition. The inflection point of these transition curves ($T_m$) was calculated by fitting the curves using a Boltzmann equation.

A $T_m$ 70.2° C. and 70.7° C. dependent of the protein concentration was obtained for the model protein in PBS Buffer. Addition of trehalose alone to the protein solution resulted in a thermal shift between 2 to 3° C. with a slight decrease in the higher concentration range of trehalose (FIG. 1A, G and Table 1). In contrast, already the addition of chitosan alone led to a more remarkable stabilizing effect on the thermal denaturation profile of the model protein. The thermal shift of the $T_m$ with chitosan was between 3 to 5° C. with an increase with increasing chitosan concentrations (FIG. 1B, G and table 1). The thermal shift of the model protein between 2.5 and 3.2° C. with an excipient mixture based on the SPS platform technology was approximately comparable with the stabilizing effect of trehalose in this assay (FIG. 1C, G and table 1). After addition of chitosan to this excipient mixture based on the SPS platform technology, a pronounced concentration-dependent increase of the thermal shift was found. Greater than 3° C. in the small concentration range to approximately 9° C. in the higher concentration range was determined for this excipient mixture (FIG. 1E, G and table 1). In the case of the addition of trehalose to the SPS based excipient mixture a concentration dependent increase of the thermal shift from 2.5° C. to 6.5° C. was found (FIG. 1D, G and table 1). Further addition of chitosan to the mixture of SPS and trehalose led to additional enhanced thermal shifts in a concentration dependent manner. The $T_m$ of the model protein increases with increasing concentrations of the mixture from 2.7 to nearly 11° C., suggesting a synergistic stabilizing effect of chitosan in combination with the different excipient mixtures (FIG. 1F, G and table 1). For the further study considering the stability of the H1N1 split vaccine, the mixture of chitosan, SPS and trehalose with the highest concentration and the corresponding highest thermal shift of 11° C. was applied.

EXAMPLE 3: STRUCTURAL ANALYSIS

To correlate the functional activity of the SPS-formulated vaccines with the retention of structural integrity, SDS-PAGE migration patterns of these samples were compared with the positive control (FIG. 2). Non-reducing and reducing SDS-PAGE analysis of original Pandemrix indicated typical migration patterns for highly purified split vaccines. Non-reducing SDS-PAGE showed six separated bands in the case of the original Pandemrix (FIG. 2A).

Because of the highly hydrophobic nature of the integral membrane protein hemagglutinin and the resulting high susceptibility to form soluble aggregates in solution and protein complexes with the other protein components, an assignment of the single bands to single components is very difficult. The lack of the protein bands migrating at molecular weights of 200 kDa and between 200 and 116.5 kDa under reducing conditions indicated that the oligomeric forms observed under non-reducing conditions were disulphide linked oligomers of HA0 particularly dimers and trimers (FIGS. 2A and B). The bands at approximately 65 kDa in the non-reducing SDS-PAGE may correspond to the likewise disulphide linked HA0 monomers, not visualised by reducing SDS-PAGE. The band at approximately 55.4 kDa could correspond to smaller amounts of HA1 in complex with the nucleoprotein. A small band between 31 and 21.5 kDa may correspond to the protein complex of HA2 and the matrix protein M1. The small amount of degradation of the disulphide-linked HA0 and the dimer and trimer, respectively could be a consequence of the sample preparation for the non-reducing gel—heating of the samples for 10 min at 90° C. leading to maximum binding of SDS to the protein (FIG. 2A). Upon the loss of the bands corresponding to the disulphide-linked HA0 monomer and the hemagglutinin dimer and trimer two prominent bands in the reducing SDS-PAGE may correspond to the HA1 and HA2 subunits of hemagglutinin in complex with nucleoprotein and matrix protein, respectively (FIG. 2B).

It is known from literature that nucleoproteins and matrix proteins, being present in the split vaccine formulation, can interfere with the detection of hemagglutinin [26, 31]. In the case of the liquid SD M before spray-drying the same migration pattern as the positive control in the non-reducing as well as in the reducing SDS-PAGE was found (FIGS. 2A and B). In contrast, SD M showed a considerable loss of band intensity corresponding to the main antigenic components of the split vaccine (data not shown), matching the pronounced loss of functional integrity in the HA-assay. Subsequent β-irradiation of this formulation at 25 kGy led to almost complete loss of the typical migration pattern, suggesting substantial fragmentation of the protein constituents (FIGS. 2A and B). From the migration patterns of the SPS formulated vaccines it can be seen that the chitosan-containing preparations liquid SPS T final (before SD), SD SPS T final and SD SPS T final 25 kGy (FIGS. 2A and B, lanes 2 to 4) resulted in a long smear overlaying individual bands. It is well-known that chitosan can bind to lipids [29]. Thus, chitosan-HCl might bind to the residual fragments of the lipid membrane of the split vaccine in these formulations, which may cause this effect. There was no loss of any protein band and particularly of hemagglutinin in SPS protected vaccines after spray-drying and irradiation.

EXAMPLE 4: ANALYSIS OF STORAGE STABILITY

SDS PAGE Electrophoresis

After storage times of one month (FIGS. 2C and D; lanes 2 to 5) and three months (FIGS. 2E and F; lanes 2 to 5) at 2 to 8° C. and at 25° C. (rH 60%), the analysis showed no changes in the migration pattern of the SD SPS T final and SD SPS T final 25 kGy compared to the corresponding migration pattern at t=0 (FIGS. 2A and B; lanes 2 to 4). In the case of SD M 25 kGy, storage for 1 and 3 months at 25° C. (rH 60%) led to a further loss of residual protein components of the split vaccine (FIGS. 2C, D, E, and F, lane 7) compared to storage at 2 to 8° C. (FIGS. 2C, D, E, and F; lane 6) and time point t=0 (FIGS. 2A and B; lane 7). This shows that the SPS-stabilised spray dried and particularly the irradiated formulation remained stable not only upon refrigerated storage, but also at 25° C., 60% rH demonstrating increased thermo stability.

Dynamic Light Scattering (DLS)

DLS data displays the size of colloidal components and aggregates. As visible in FIG. 4*a*, original Pandemrix consists of colloidal components of a certain size distribution, but no large aggregates were visible. After spray drying, aggregates were visible for the SD M formulation as indicated by the second peak at around 5000 nm, but not for the SD SPS T final formulation (FIGS. 4*a* and *b*). After irradiation a slight increase in aggregation can be seen for the SD SPS T final 25 kGy formulation (FIGS. 4*a* and *d*). On storage for one month and three months, respectively, the spray dried and the subsequently irradiated formulations with SPS did not show an increase in aggregation irrespective of the storage conditions as shown in FIGS. 4*c* and *d*. This indicates that no destabilising processes take place over storage time which would increase aggregation upon redispersion.

Size Exclusion Chromatography

In size exclusion chromatography the highly hydrophobic nature of the protein led to elution as protein complexes. SEC chromatograms are shown in FIG. 5. The first peak at about 11 ml in the original Pandemrix could be assigned to a high molecular weight complex of the protein constituents>500 kDa. The second peak at 16 ml may represent the HA trimer of 255 kDa; it became larger in the SD M and is heavily increased in the SD M 25 kGy (FIG. 5*a*). The third peak could be the HA monomer, which is totally lost in the corresponding irradiated formulation SD M 25 kGy (FIG. 5*a*). The SD SPS T final exhibits the same peaks of the trimer and the monomer, but lost the high molecular weight complex (FIGS. 5*a* and *c*) indicating a stable formulation.

In contrast, SD M 25 kGy showed changes in the trimer peak area, especially upon storage at 25° C./60% rH for 1 and 3 months (FIGS. 5*a* and *b*) indicating that the antigen was not stabilised properly leading to increased aggregation upon redispersion. SEC chromatographs (FIGS. 5*c* and *d*) showed no change in the SD SPS T final or the SD SPS T final 25 kGy formulation after storage for 1 and 3 months at either storage condition compared to the freshly prepared formulation.

Water Content

As storage stability was performed under tightly sealed conditions, a remarkable change would indicate an improper sealing. No such effect was observed (FIG. 6).

EXAMPLE 5: IN VIVO ANALYSIS

Throughout the experimental period all animals maintained weight, haemoglobin level and body temperature within the expected range for the species. No adverse reactions were observed at the site of injection and no lymphadenopathy was detected by palpation. 21 days post-vaccination, all animals in groups 4 and 5, and five out of six animals in group 2, had sero-converted as shown by an HAI titre≥40 (FIG. 3*a*). In contrast, all six animals in group 3 (SD M 25 kGy) remained sero-negative (HAI titres≤20). These observations were confirmed by MN titres which showed group 3 sera to be equivalent to mock-vaccinated control sera (MN titres 40-80), with all animals in groups 2, 4 and 5 showing MN titres of between 160 and 5120 (FIG. 3b).

Figure 3:
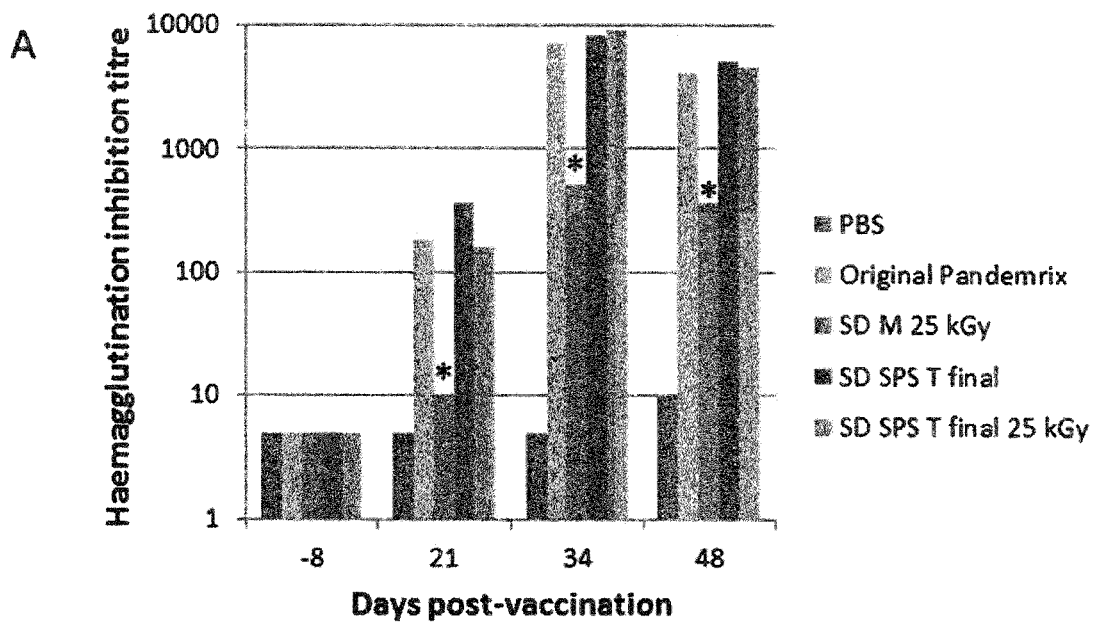
Figure 3:
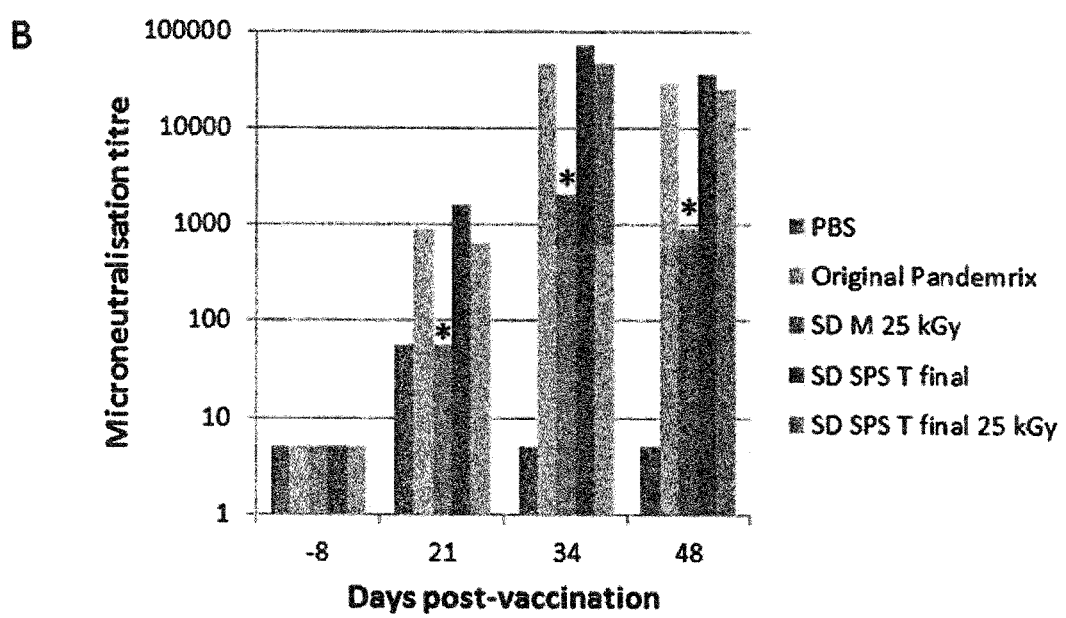
Figure 4:
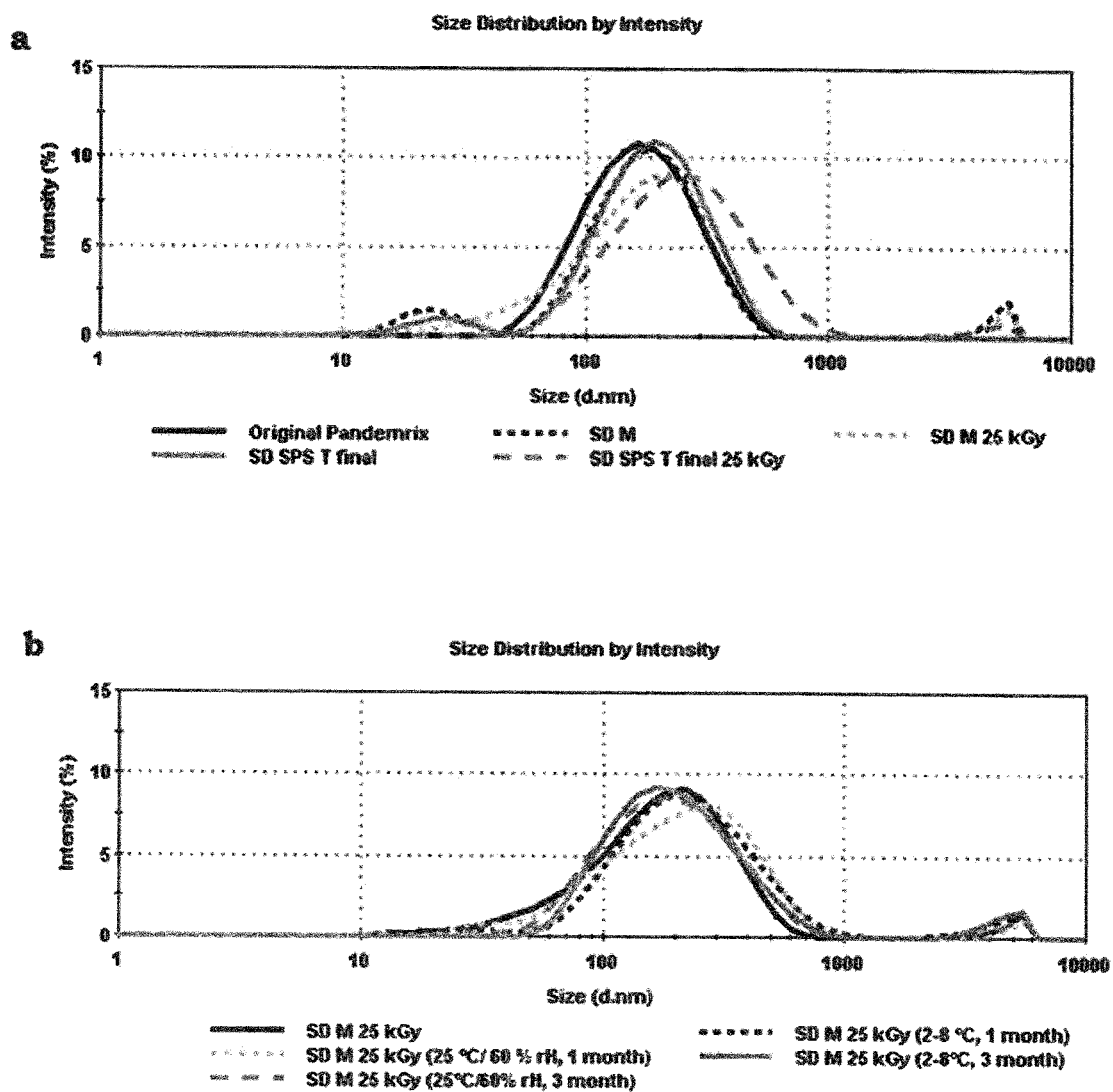
Figure 4:
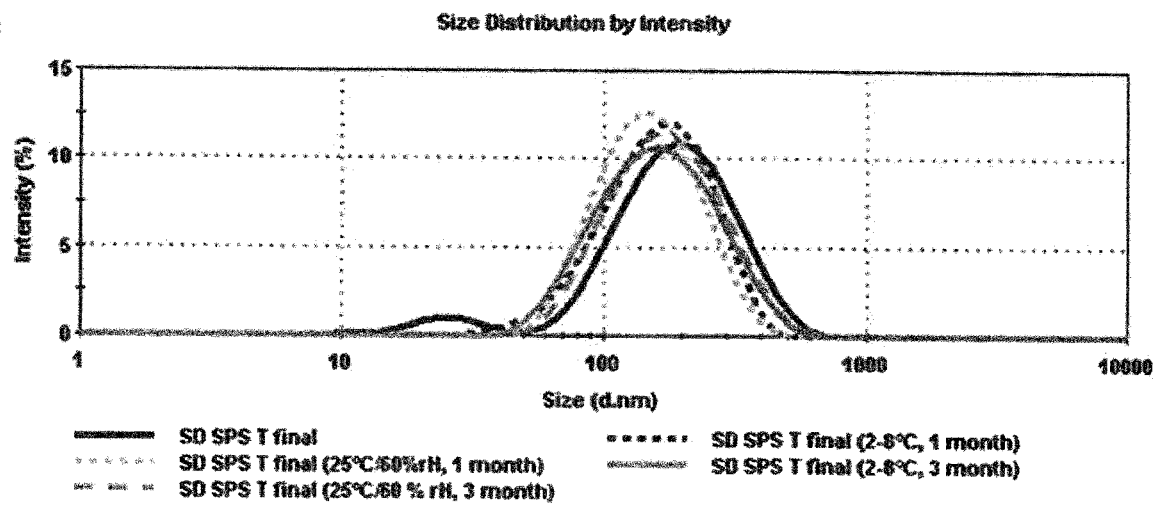
Figure 4:
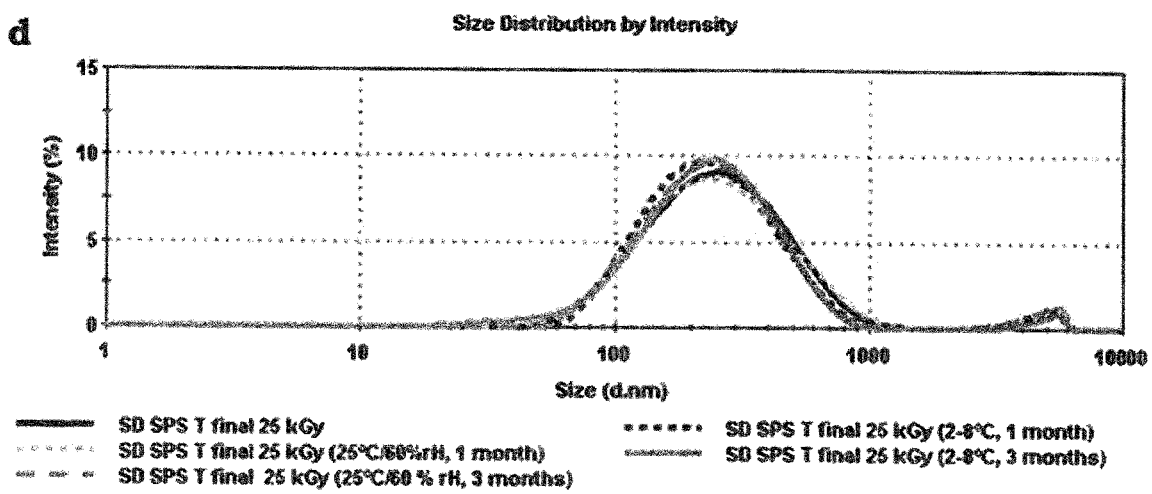
Figure 5:
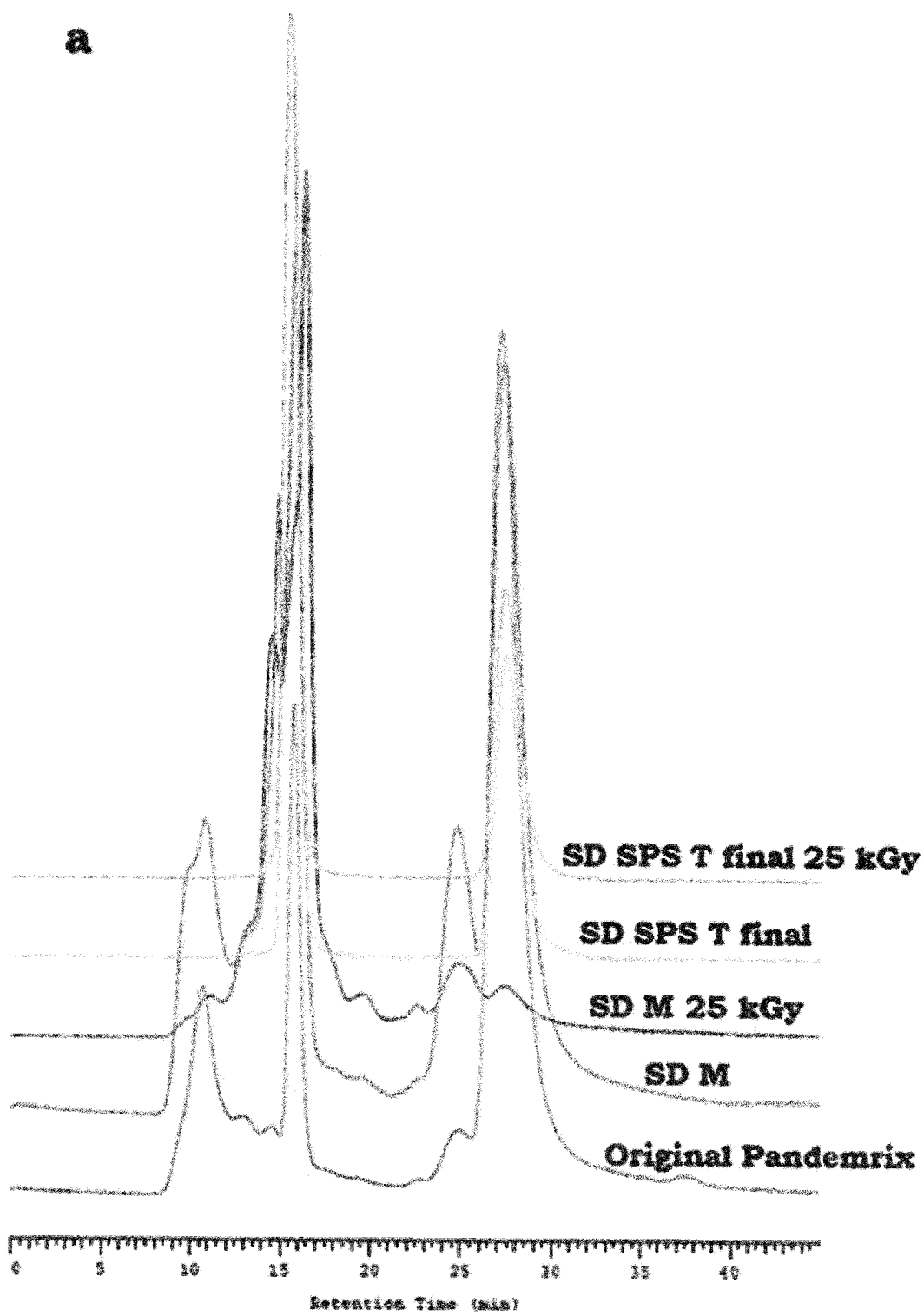
Figure 5:
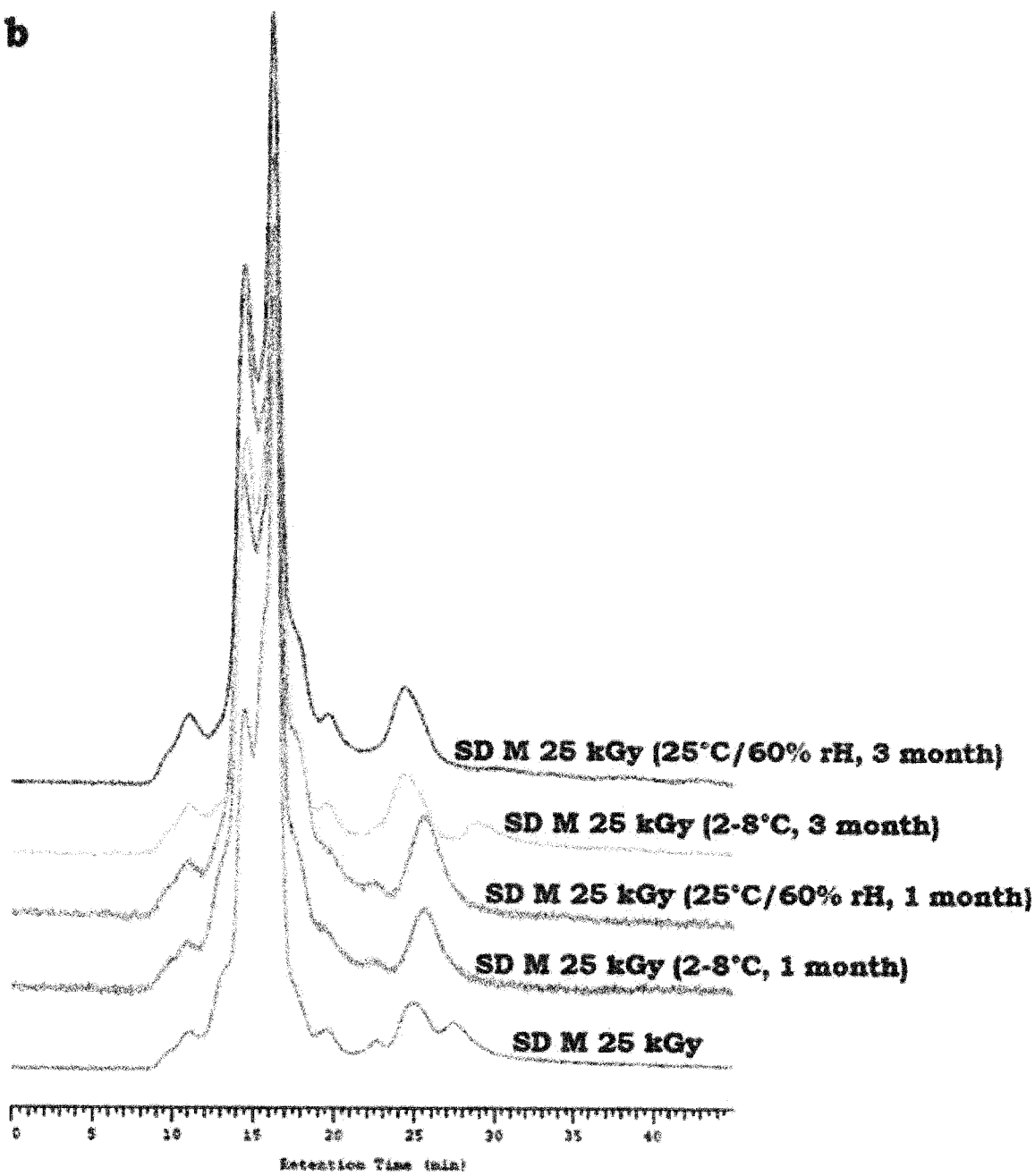
Figure 5:
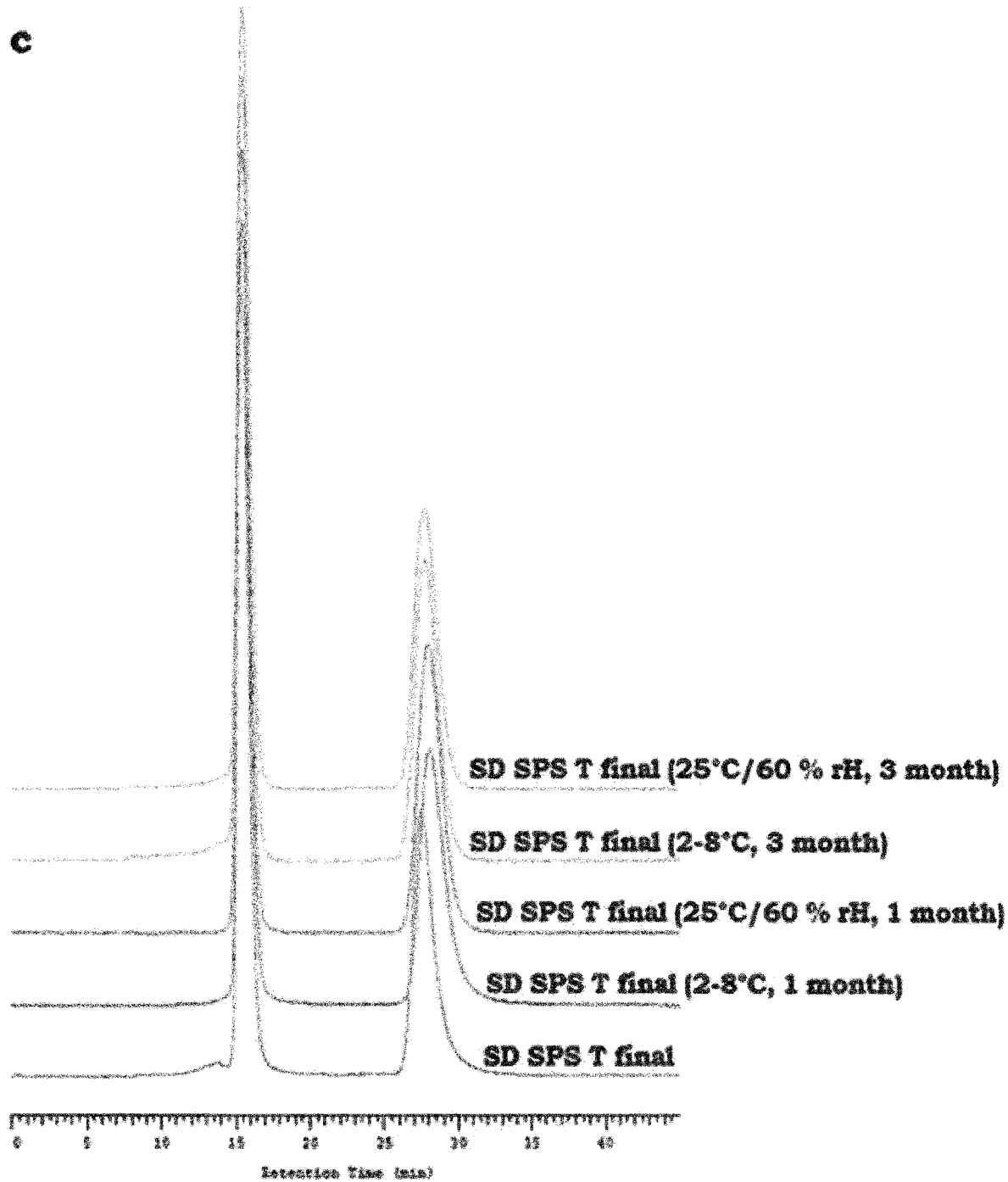
Figure 5:
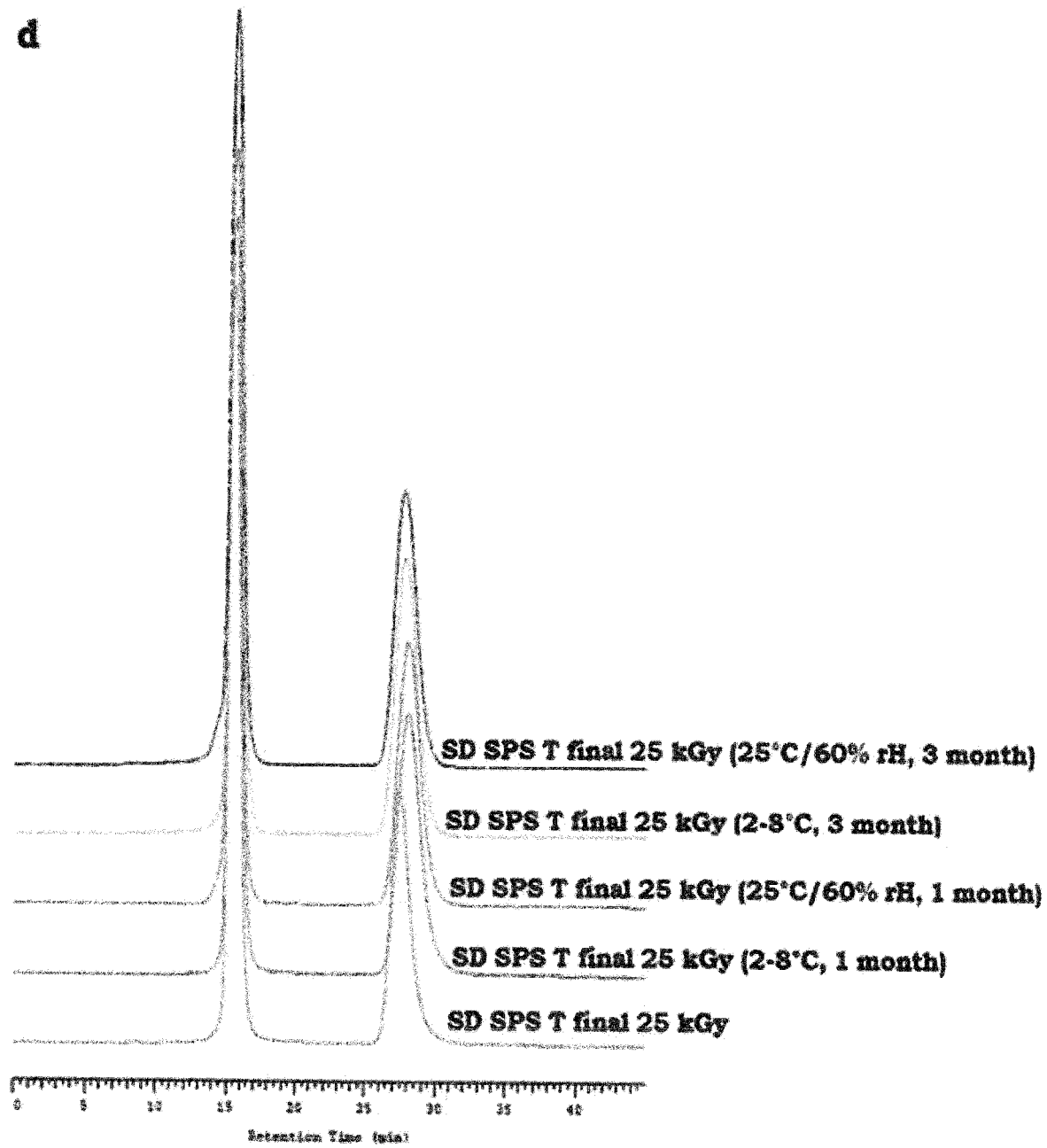
Figure 6:
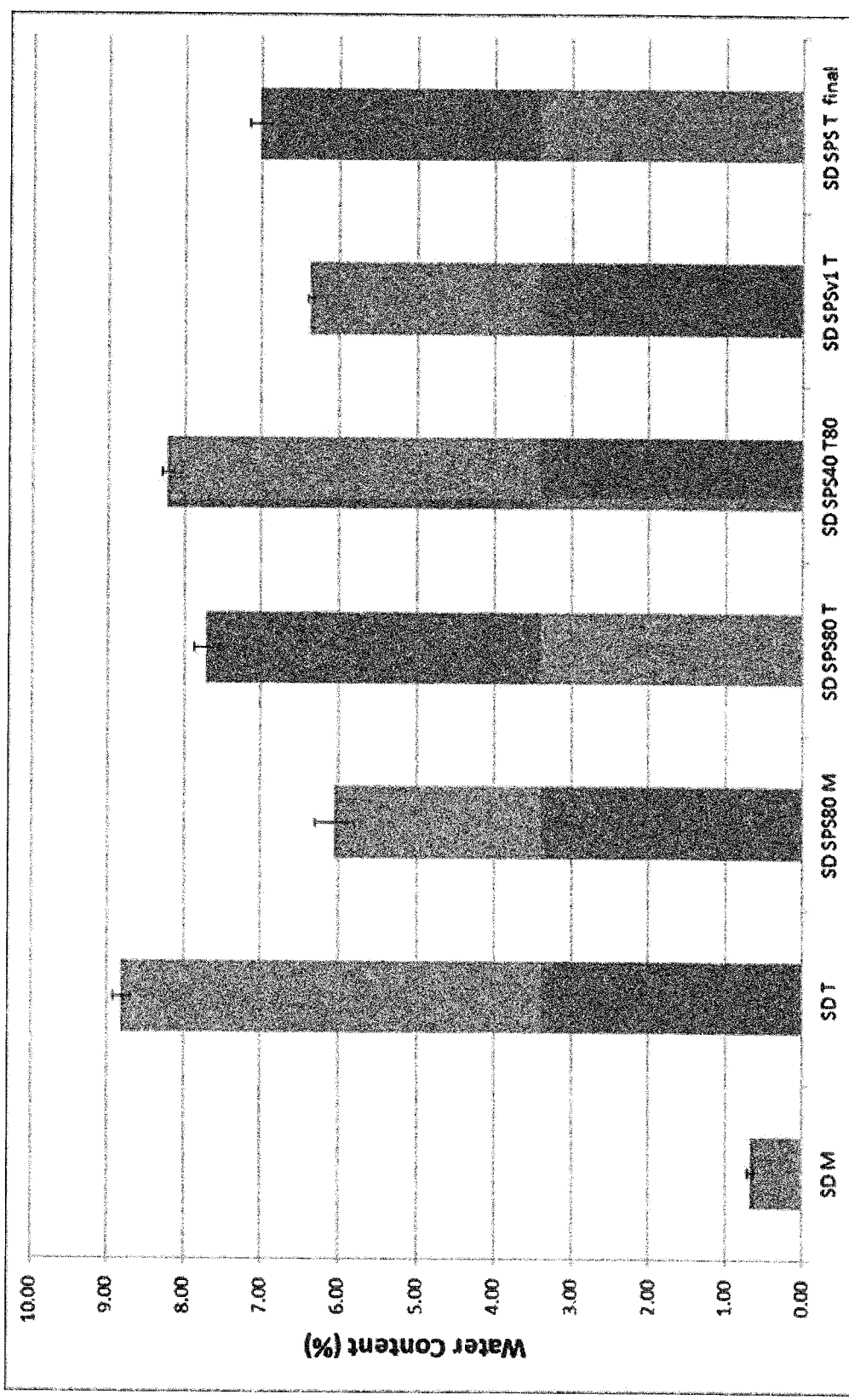
Figure 7:
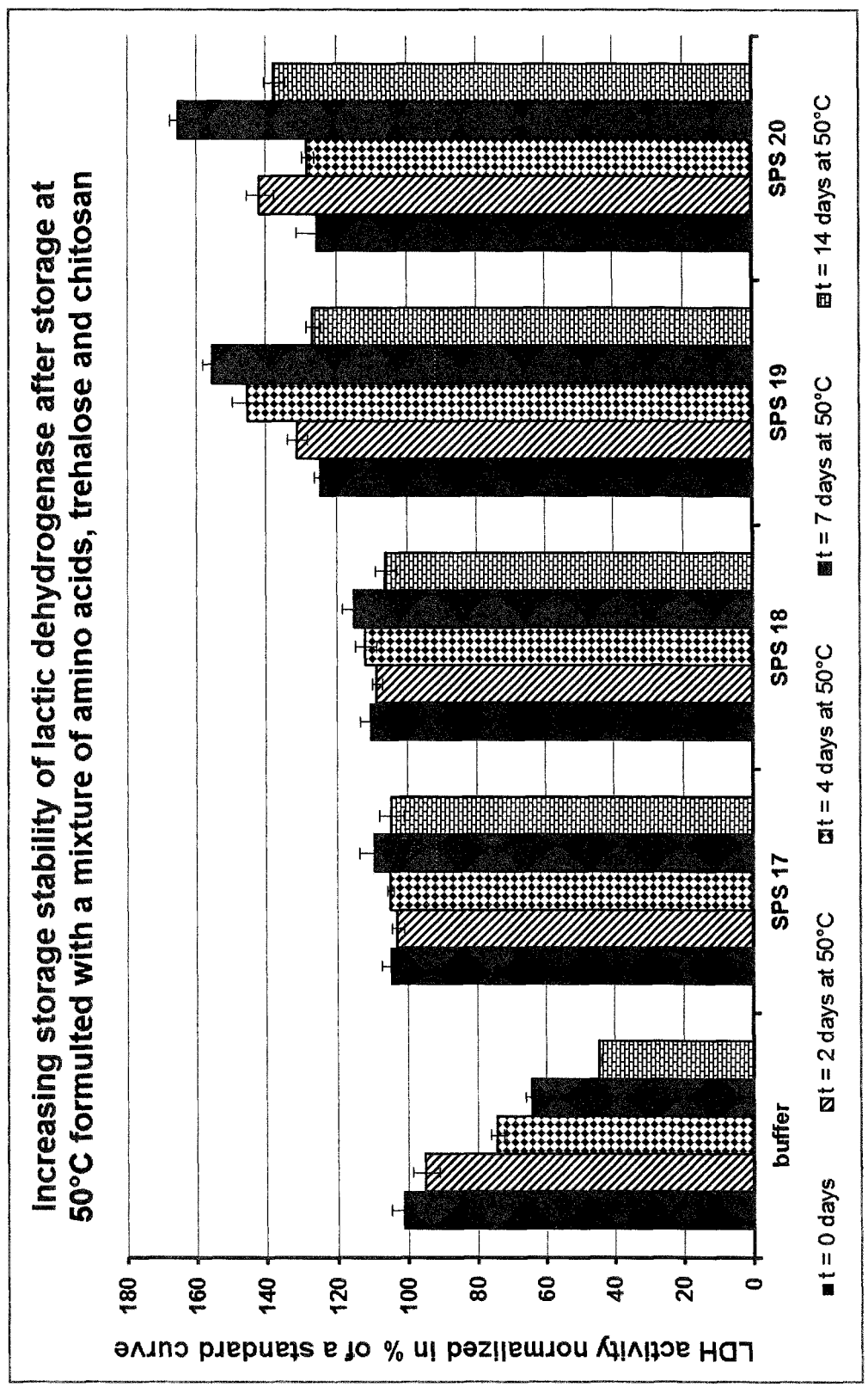
Figure 8:
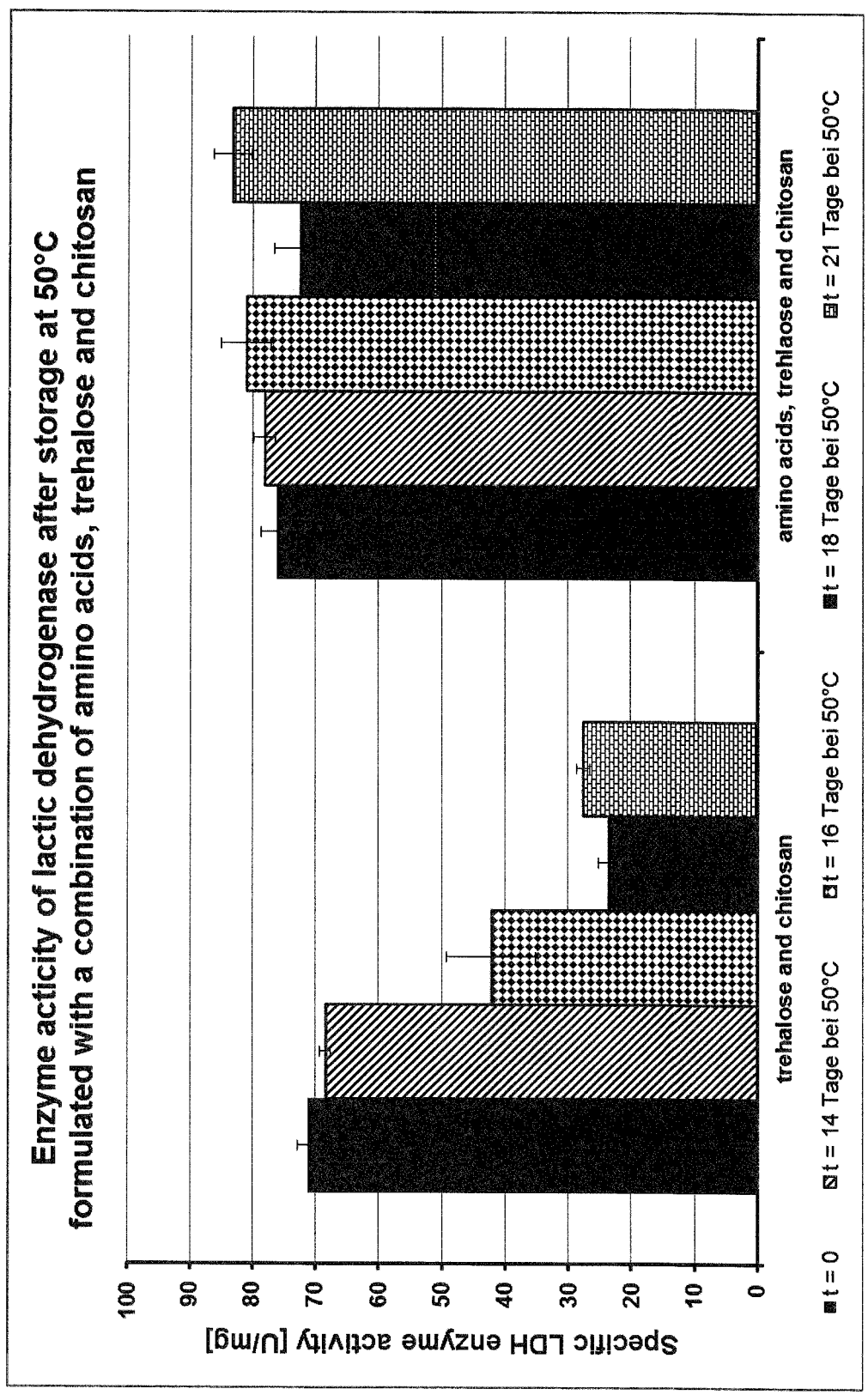
Figure 9:
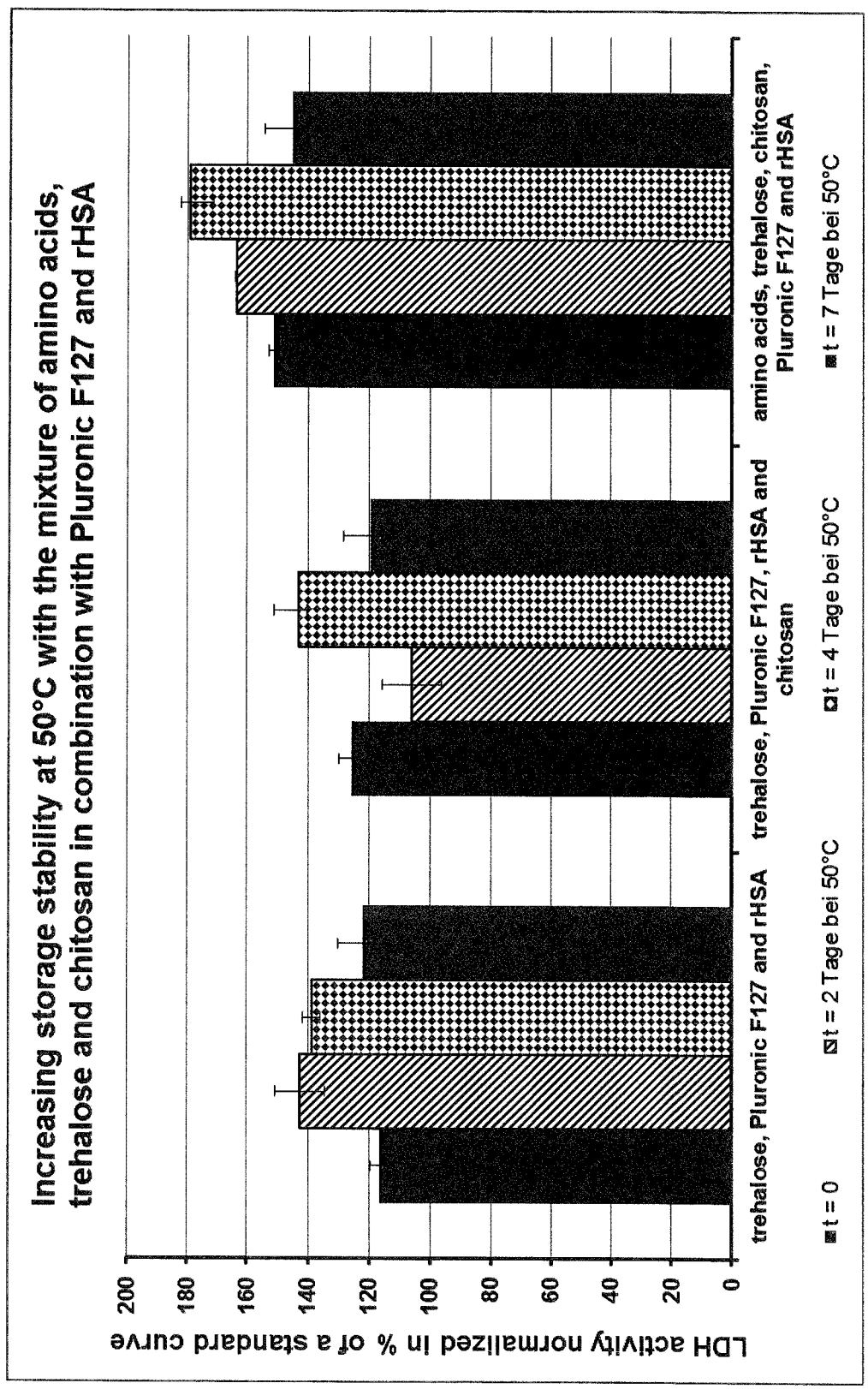

All animals then received a booster vaccination 28 days after primary vaccination, and sera were taken for analysis 6 and 20 days post-boost. Following boost, all animals in group 3 showed seroconversion by HAI and MN titres. However, mean titres for group 3 remained significantly lower than mean titres of groups 2, 4 and 5 in both assays (FIG. 3). Mean titres of groups 2, 4 and 5 were not significantly different from one another. Mock-vaccinated animals were boosted with PBS and did not sero-convert. These data demonstrate that spray-drying and irradiation led to >10-fold reduction in mean HAI titre and >15-fold reduction in mean MN titre in the absence of protection; whereas in the presence of the inventive solution, there was no significant reduction in titre due to irradiation. Furthermore, spray-drying of vaccine in the presence of the inventive solution had no detrimental effect on immunogenicity compared to untreated vaccine.

EXAMPLE 6: STORAGE STABILITY OF THE MODEL ENZYME LACTIC DEHYDROGENASE (LDH) AT 50° C. IN THE LIQUID STATE

Further experiments were carried out to show the influence of individual compounds on the stability of proteins during storage. In addition, a direct comparison with the results described in WO 2009/014774 was carried out, where a combination of chitosan with trehalose, Pluronic F127 and rHSA was allegedly shown to decrease the antigen titre loss upon incubation at 37° C. However, the presence of rHSA in the samples renders it impossible to analyse the effect on the above employed split virus preparation, as the rHSA would present in an SDS-PAGE analysis at the same band size as hemagglutinin. To nonetheless enable a direct comparison, the following experiments were carried out using the model enzyme lactic dehydrogenase (LDH) as proof of concept. LDH is a commonly employed model protein employed in the development of spray dried formulations, freeze drying and the effect of storage on this enzyme can conveniently be analysed in enzyme assay readouts.

Materials and Methods

Lactic dehydrogenase (LDH; Sigma-Aldrich, Munich, Germany) was recombinantly expressed in *E. coli* and was used as the model protein, for the reasons detailed above. A 50 mg/ml stock solution of LDH was prepared by dissolving the lyophilized powder of the enzyme in 10 mM sodium phosphate buffer pH 7.5. For the preparation of the formulation variants the LDH stock solution was further diluted to an enzyme concentration of 1 mg/ml with the respective formulations. The LDH formulations were subsequently incubated at 50° C. for 21 days and the enzyme activity of lactic dehydrogenase was measured at the indicated time points (t=0; 2; 4; 7; 14; 16; 18; and 21 days).

LDH enzymatic activity was determined by monitoring the decrease in absorbance of the reduced cofactor NADH at a wavelength of 340 nm and at a temperature of 22° C. upon the enzymatic reaction of pyruvate to lactate. Before measuring the activity, the formulations were diluted to a concentration of 37.5 µg/ml with 100 mM sodium phosphate buffer pH 7.5. A reaction mixture of 790 µl sodium phosphate buffer pH 7.5; 100 µl pyruvate stock solution (20 mM) and 100 µl NADH stock solution (1 mM) was prepared and the enzymatic reaction was started by addition of 10 µl LDH dilution (37.5 µg/ml).

Results

The enzymatic activity of LDH after liquid storage at 50° C. was measured at various time points. FIG. 7 summarises the results obtained for LDH storage after formulation with one of 4 different SPS variants in comparison to a buffer formulation. SPS 17 is a mixture of 4 amino acids, SPS 18 is a mixture of 4 amino acids with trehalose, SPS 19 is a mixture of 4 amino acids in combination with chitosan and SPS 20 is a mixture of 4 amino acids in combination with trehalose and chitosan.

As is shown in FIG. 7, when employing only a buffer formulation, there was a significant loss of activity upon storage at 50° C. In contrast, employing any of the 4 SPS variants protected LDH from such a loss of activity. Moreover, the addition of chitosan in both cases (see SPS 19 and SPS 20) increased the enzymatic activity of LDH upon liquid storage compared to the same SPS formulations without chitosan (SPS 17 and SPS 18).

FIG. 8, left group of bars, shows that a mixture of trehalose and chitosan alone, without amino acids, resulted in a dramatic loss function of the enzyme after liquid storage at 50° C. for 16; 18 and 21 days. The addition of amino acids to this mixture of trehalose and chitosan, however, was capable of leading to the retention of the enzymatic function during liquid storage of LDH at 50° C. up to 21 days. For a direct comparison with the results described in WO 2009/014774, the main components of WO 2009/014774, namely Pluronic F127 and rHSA, were combined with either trehalose, or with trehalose and chitosan, or with amino acids, trehalose and chitosan. As is shown in FIG. 9, right group of bars, the mixture of amino acids, trehalose and chitosan with Pluronic F127 and HSA led to an increase of the LDH activity between 20 and 40% after storage at 50° C. as compared to a mixture of Pluronic F127 and HSA with either trehalose alone (left group of bars) or with trehalose and chitosan (middle group of bars).

Tables:

TABLE 1

Calculated midpoints of thermal denaturation $T_m$ from the thermal denaturation plots corresponding to the model protein 300 µg/ml in buffer and in the analysed excipient mixtures in different concentrations (order C1 to C8 with increasing concentration).

| Formulation | C 1 $T_m$ [° C.] | C 2 $T_m$ [° C.] | C 3 $T_m$ [° C.] | C 4 $T_m$ [° C.] | C 5 $T_m$ [° C.] | C 6 $T_m$ [° C.] | C 7 $T_m$ [° C.] | C 8 $T_m$ [° C.] |
|---|---|---|---|---|---|---|---|---|
| PBS | 70.7 | 70.7 | 70.7 | 70.7 | 70.7 | 70.7 | 70.7 | 70.7 |
| trehalose | 73.7 | 73.2 | 73.7 | 73.5 | 71.9 | 72.7 | 72.8 | 72.8 |
| chitosan | 73.9 | 74.0 | 73.9 | 74.0 | 74.2 | 74.9 | 75.9 | 75.4 |
| SPS | 73.2 | 73.1 | n.d. | 73.7 | 73.5 | 73.5 | 73.3 | 73.8 |
| SPS + trehalose | 72.3 | n.d. | 73.0 | 74.4 | 75.7 | 76.6 | n.d. | 76.0 |
| SPS + chitosan | 73.6 | 73.9 | 73.9 | 74.3 | 75.6 | 77.5 | n.d. | 79.3 |
| SPS + trehalose + chitosan | 73.4 | 73.7 | 73.2 | 74.2 | 76.0 | 78.4 | 80.9 | 81.5 |

TABLE 2

Calculated midpoints of thermal denaturation $T_m$ from the thermal denaturation plots corresponding to the model protein 600 μg/ml in buffer and in the analysed excipient mixtures in different concentrations (order C1 to C8 with increasing concentration).

| Formulation | C 1 $T_m$ [° C.] | C 2 $T_m$ [° C.] | C 3 $T_m$ [° C.] | C 4 $T_m$ [° C.] | C 5 $T_m$ [° C.] | C 6 $T_m$ [° C.] | C 7 $T_m$ [° C.] | C8 $T_m$ [° C.] |
|---|---|---|---|---|---|---|---|---|
| PBS | 70.2 | 70.2 | 70.2 | 70.2 | 70.2 | 70.2 | 70.2 | 70.2 |
| trehalose | 73.6 | 73.5 | 74.2 | 74.2 | 73.5 | 73.0 | 72.6 | 73.1 |
| chitosan | 73.6 | 73.7 | 73.4 | 73.1 | 73.3 | 74.0 | 75.2 | 75.4 |
| SPS | 73.1 | 72.9 | 72.8 | 73.9 | 72.8 | 72.4 | 72.1 | 73.0 |
| SPS + trehalose | n.d. | 72.8 | 73.1 | n.d. | 74.0 | 74.4 | 74.8 | 75.8 |
| SPS + chitosan | 73.5 | 73.6 | 73.3 | 74.1 | 75.5 | 78.1 | n.d. | 78.9 |
| SPS + trehalose + chitosan | 73.3 | 73.1 | 73.2 | 73.8 | 75.7 | 77.6 | 80.4 | 81.5 |

TABLE 3

Overview of formulation variants. Formulations for the in vivo study are marked with an asterisk.

| Pandemrix formulations | SPS (mg/mL) | HA (μg/mL) | matrix (mg/mL) | further components/variations | irradiation |
|---|---|---|---|---|---|
| Original Pandemrix* | — | 15 | — | — | — |
| SD M | — | 15 | Mannitol, 160 | — | No<br>Yes* 25 kGy<br>Yes 40 kGy |
| SD T | — | 15 | Trehalose, 160 | — | No<br>Yes 25 kGy<br>Yes 40 kGy |
| SD SPS80 M | 80 | 15 | Mannitol, 160 | — | No |
| SD SPS80 T | 80 | 15 | Trehalose, 160 | — | No<br>Yes 25 kGy<br>Yes 40 kGy |
| SD SPS80 T80 | 80 | 15 | Trehalose, 80 | — | No |
| SD SPS40 T80 | 40 | 15 | Trehalose, 80 | — | No<br>Yes 25 kGy<br>Yes 40 kGy |
| SD SPSv1 T | 80 | 15 | Trehalose, 160 | Variation of SPS (no hygroscopic amino acids) | No<br>Yes 25 kGy<br>Yes 40 kGy |
| SD SPS T final | 80 | 15 | Trehalose, 160 | 2 mg/ml GA + 2 mg/ml Chitosan-HCl | No*<br>Yes* 25 kGy |

TABLE 4

Spray-drying parameters used.

| Parameters | Values |
|---|---|
| Two fluid nozzle | 1.5 mm inner diameter |
| Inlet air temperature | 120 (° C.) |
| Aspirator air flow | 35 ($m^3$/h) = 100% |
| Flow rate | 5-6 (ml/min) |
| Spray flow rate | 470 L/h |
| Outlet air temperature | 50-55 (° C.) |

REFERENCES

[1] Scherließ R. Delivery of antigens used for vaccination—recent advances and challenges. Therapeutic Delivery 2011; 2(10):1351-68.

[2] WHO. GIVS: Global Immunization Vision and Strategy. Geneva: WHO; 2005.

[3] Amorij J-P, Huckriede A, Wilschut J, Frijlink H W, Hinrichs W L J. Development of Stable Influenza Vaccine Powder Formulations: Challenges and possibilities. Pharm Res 2008; 25(6):1256-73.

[4] Hasija M, Li L, Rahman N, Ausar S F. Forced degradation studies: an essential tool for the formulation development of vaccines. Vaccine: Development and Therapy 2013(3):11-33.

[5] Brandau D T, Jones L S, Wiethoff C M, Rexroad J, Middaugh C R. Thermal Stability of Vaccines. J Pharm Sci 2003; 92(2):218-31.

[6] Taneja S, Ahmad F. Increased thermal stability of proteins in the presence of amino acids. Biochem J 1994; 303:147-53.

[7] Wang W. Lyophilization and development of solid protein pharmaceuticals. International Journal of Pharmaceutics 2000; 203:1-60.

[8] Amorij J-P, Meulenaar J, Hinrichs W L J, Stegmann T, Huckriede A, Coenen F, et al. Rational design of an influenza subunit vaccine powder with sugar glass technology: Preventing conformational changes of hemagglutinin during freezing and freeze-drying. Vaccine 2007; 25:6447-57.

[9] Vehring R. Pharmaceutical Particle Engineering via Spray Drying. Pharm Res 2008; 25:999-1022.

[10] Maury M, Murphy K, Kumar S, Mauerer A, Lee G. Spray-drying of proteins: effects of sorbitol and trehalose on aggregation and FT-IR amide I spectrum of an immunoglobulin G. EJPB 2005; 59:251-61.

[11] Elkordy A A, Forbes R T, Barry B W. Stability of crystallised and spray-dried lysozyme. International journal of pharmaceutics 2004; 278(2):209-19.

[12] Saluja V, Amorij J-P, Kapteyn J C, de Boer A H, Frijlink H W, Hinrichs W L J. A comparison between spray drying and spray freeze drying to produce an influenza subunit vaccine powder for inhalation. J Controlled Release 2010; 144:127-33.

[13] Abdul-Fattah A M, Truong-Le V, Yee L, Pan E, Ao Y, Kalonia D S, et al. Drying-Induced Variations in Physico-Chemical Properties of Amorphous Pharmaceuticals and Their Impact on Stability II: Stability of a Vaccine. Pharmaceutical Research 2007; 24(4):715-27.

[14] Lal M. Technologies for the Development of Thermostable Vaccines: PATH; 2013.

[15] Son Y-J, McConville J T. Development of a Standardized Dissolution Test for Inhalable Formulations. Respiratory Drug Delivery; 2008; Scottsdale, Ariz., USA: DHI; 2008. p. 927-30.

[16] Rathore N, Rajan R S. Current perspectives on stability of drug products during formulation, fill and finish operations. Biotechnol Prog 2008; 24:504-14.

[17] Shire S J. Formulation and manufacturability of biologics. Current Opinion in Biotechnology 2009; 20:708-14.

[18] Bhamra K, Harrison P, Philipps J, Hale G. Aseptic vial filling. Methods Mol Med 2000; 40:313-7.

[19] Zbikowska H M, Nowak P, Wachowicz B. Protein modification caused by a high dose of gamma irradiation in cryo-sterilized plasma: Protective effects of ascorbate. Free Radical Biology & Medicine 2006; 40:536-42.

[20] Garrison W M, Jayko M E, Bennett W. Radiation-induced oxidation of protein in aqueous solution. Radiat Res 1962; 16:483-502.

[21] Kapoor S, Priyadarisini K I. Protection of Radiation-Induced Protein Damage by Curcumin. Biophys Chem 2001; 92:119-26.

[22] De Groot A S, Scott D W. Immunogenicity of protein therapeutics. TRENDS in Immunology 2007; 28(11):482-90.

[23] Niesen F H, Berglund H & Vedadi M. The use of differential scanning fluorimetry to detect ligand interactions that promote protein stability. Nature Protocols 2007; 2(9): 2212-2221

[24] Philips K & Hernandez de la Peña. The combined use of the Thermofluor Assay and ThermoQ Analytical Software for the Determination of Protein Stability and Buffer Optimization as an Aid in Protein Crystallization. Curr. Protoc. Mol. Biol. 2011; 94: 10.28.1-10.28.15

[25] Li X., Min M., Du N., Gu Y., Hode T., Naylor M., Chen D., Nordquist R E., Chen Wr. Chitin, Chitosan, and Glycated Chitosan Regulate immune Responses: The Novel Adjuvant for Cancer Vaccine. Clinical and Developmental Immunology. 2013; 2013: 1-8

[26] Garcia-Cañas V, Lorbetskie B, Cyr T D, Hefford M A, Smith S, Girard M. Approach to the profiling and characterization of influenza vaccine constituents by the combined use of size-exclusion chromatography, gel electrophoresis and mass-spectroscopy. Biologicals 2010; 38(2): 294-302.

[27] Riese P., Schulze K., Ebensen T., Prochnow B., Guzman C A. Vaccine Adjuvants: Key Tools for innovative Vaccine Design: Current Topics in Medicinal Chemistry. 2013; 13: 1-19.

[28] Lee L-Y., Khor E., Koo O. J Biomed Mater Res (Appl Biomater) 1998; 43: 282-290.

[29] Wydro P, Krajewska B, Hac-Wydro K. Chitosan as a Lipid Binder: A Langmuir Monolayer Study of Chitosan-Lipid Interactions. Biomacromolecules 2007; 8:2611-7.

[30] Aspden T J, Masen J T D, Jones N S, Lowe J, Skaugrud O, Ilium L. Chitosan as a Nasal Delivery System: The Effect of Chitosan Solutions on in Vitro and in Vivo Mucociliary Transport Rates in Human Turbinates and Volunteers. J Pharm Sci 1997; 86(4):509-13.

[31] Davis S S, Ilium L. Absorption Enhancers for Nasal Drug Delivery. Clin Pharmacokinet 2003; 42(13):1107-28.

[32] Ilium L, Farraj N F, Davis S S. Chitosan as a Novel Nasal Delivery System for Peptide Drugs. Pharm Res 1994; 11(8):1186-9.

[33] Illum L, Jabbal-Gill I, Hinchcliffe M, Fisher A N, Davis S S. Chitosan as a novel nasal delivery system for vaccines. Advanced Drug Delivery Reviews 2001; 51:81-96.

[34] Liu X F, Guan Y L, Yang D Z, Li Z, De Yao K J. Antibacterial action of chitosan and carboxymethylated chitosan. J Appl Polym Sci. 2001; 79(7): 1324-1335.

The invention claimed is:

1. A method for producing stabilised vaccines, the method comprising:
    (a) mixing antigens with a solution comprising:
        (i) chitosan;
        (ii) at least three different amino acids; and
        (iii) a sugar; and
    (b) drying the mixture obtained in (a).

2. The method of claim 1, wherein the at least three amino acids are selected from at least two different groups selected from
    (a) amino acids with nonpolar, aliphatic R groups;
    (b) amino acids with polar, uncharged R groups;
    (c) amino acids with positively charged R groups;
    (d) amino acids with negatively charged R groups; and
    (e) amino acids with aromatic R groups.

3. The method of claim 1, wherein the solution comprises at least one amino acid selected from each group of
    (a) an amino acid with nonpolar, aliphatic R groups;
    (b) an amino acid with polar, uncharged R groups;
    (c) an amino acid with positively charged R groups;
    (d) an amino acid with negatively charged R groups; and
    (e) an amino acid with aromatic R groups.

4. The method according to claim 1, wherein the solution comprises at least the amino acids selected from:
    (a) alanine, glutamate, lysine, threonine and tryptophan;
    (b) aspartate, arginine, phenylalanine, serine and valine;
    (c) proline, serine, asparagine, aspartate, threonine, phenylalanine;
    (d) tyrosine, isoleucine, leucine, threonine, valine;
    (e) arginine, glycine, histidine, alanine, glutamate, lysine, tryptophan; and
    (f) alanine, arginine, glycine, glutamate, lysine.

5. The method according to claim 1, wherein one or more of the amino acids are selected from natural non-proteinogenic amino acids and synthetic amino acids.

6. The method according to claim 1, wherein the sugar is trehalose.

7. The method according to claim 1, wherein the solution further comprises at least one saponine.

8. The method according to claim 1, wherein the antigens are split virus antigens.

9. The method according to claim 8, wherein the split virus antigens are influenza virus antigens.

10. The method according to claim 9, wherein the influenza virus is an influenza A virus.

11. The method according to claim 9 or 10, wherein the influenza virus is an influenza A H1N1 virus.

12. The method according to claim 1, wherein the step of drying the mixture is achieved by a method selected from spray drying, lyophilisation, spray-freeze drying and air drying.

13. The method according to claim 1, wherein the dried vaccine obtained in step (b) is subsequently sterilized.

14. The method according to claim 1, wherein the vaccine is for intramuscular, subcutaneous, intradermal, transdermal, oral, peroral, nasal, and/or inhalative application.

* * * * *